United States Patent
Wong et al.

(10) Patent No.: US 6,235,263 B1
(45) Date of Patent: May 22, 2001

(54) CARBOXY-TERMINAL BRCA1 INTERACTING PROTEIN

(75) Inventors: Alexander K. C. Wong; Paul L. Bartel; David H.-F. Teng; Sean V. Tavtigian, all of Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 0 days.

(21) Appl. No.: 09/515,884

(22) Filed: Feb. 29, 2000

Related U.S. Application Data

(62) Division of application No. 08/975,703, filed on Nov. 21, 1997, now Pat. No. 6,030,832.

(51) Int. Cl.[7] .............................. A61B 5/055; C07K 1/00; A23J 1/00

(52) U.S. Cl. ............................................. 424/9.34

(58) Field of Search .......................... 424/9.34; 530/350, 530/402, 412

(56) References Cited

U.S. PATENT DOCUMENTS

| | | | |
|---|---|---|---|
| 5,622,829 | 4/1997 | King et al. ................................ | 435/6 |
| 5,654,155 | 8/1997 | Murphy et al. ........................... | 435/6 |
| 5,693,473 | 12/1997 | Shattuck-Eidens et al. ............. | 435/6 |
| 5,710,001 | 1/1998 | Skolnick et al. ......................... | 435/6 |

OTHER PUBLICATIONS

Boyd, J.M., et al. "A region in the C–terminus of adenovirus 2/5 E1a protein is required for association with a cellular phosphoprotein and important for the negative modulation of T24–ras mediated transformation, tumorigenesis and metastasis", *The EMBO Journal*, 1993; 12(2):469–478.

Callebaut, I. and Mornon, J–P "From BRCA1 to RAP1: a widespread BRCT module closely associated with DNA repair", *FEBS Letters,* 1997; 400:25–30.

Chapman, M.S. and Verma, I.M. "Transcriptional activation by BRCA1", *Nature,* Aug. 22, 1996; 382:678–679.

Chen, Y. et al. "Aberrant Subcellular Localization of BRCA1 in Breast Cancer", *Science,* Nov. 3, 1995; 270:789–791.

Chen, C–F et al. "The Nuclear Localization Sequences of the BRCA1 Protein Interact with the Importin–α Subunit of the Nuclear Transport Signal Receptor",*J. Biol. Chem.,* Dec. 20, 1996; 271(51):32863–32868.

(List continued on next page.)

*Primary Examiner*—Hankyel T. Park
(74) *Attorney, Agent, or Firm*—Rothwell, Figg, Ernst & Manbeck

(57) ABSTRACT

Recent evidence indicates that the carboxy-terminal region of the tumor suppressor protein BRCA1 is a functionally significant domain. Using the yeast two-hybrid assay and an in vitro biochemical assay, it is here shown that a protein, B112, interacts specifically with the carboxy-terminal segment of human BRCA1 from residue 1602 to 1863. A germ line truncation mutation, 1853ter, that removes the last 11 amino acids from the carboxy-terminus of BRCA1 abolishes not only the transcription activation function, but also binding to B112. The B112 protein is apparently the same as an uncharacterized protein known as CtIP, the sequence of which was previously deposited in GenBank. Screenings of a panel of 92 tumor cell lines for mutations in the B112/CtIP sequence have identified a number of missense variants, including a non-conserved lysine to glutamic acid change at codon 337 in the pancreatic cancer line, BxPC3. Taken together, these results indicate that B112/CtIP participates in a common biochemical pathway as BRCA1 and that the interaction of these two proteins may be required for the tumor suppressor function of BRCA1.

13 Claims, 2 Drawing Sheets

OTHER PUBLICATIONS

Chen, Y. et al. "BRCA1 Is a 220–kDa Nuclear Phosphoprotein That Is Expressed and Phosphorylated in a Cell Cycle–dependent Manner", *Cancer Research,* Jul. 15, 1996; 56:3168–3172.

Hakem, R. et al. "The Tumor Suppressor Gene Brca1 Is Required for Embryonic Cellular Proliferation in the Mouse", *Cell,* Jun. 28, 1996; 85:1009–1023.

Jin, Y. et al. "Cell cycle–dependent colocalization of BARD1 and BRCA1 proteins in discrete nuclear domains", *Proc. Natl. Acad. Sci. USA,* Oct. 1997; 94:12075–12080.

Koonin, E.V. et al. "BRCA1 protein products: functional motifs", *Nature Genetics,* Jul. 1996; 13:266–268.

Larson, J.S. et al. "A BRCA1 Mutant Alters $G_2$–M Cell Cycle Control in Human Mammary Epithelial Cells", *Cancer Research,* Aug. 15, 1997; 57:3351–3355.

Maldonado, E. et al. "A human RNA polymerase II complex associated with SRB and DNA–repair proteins", *Nature,* May 2, 1996; 381:86–89.

McAllister, K.A. et al. "Characterization of the Rat and Mouse Homologues of the BRCA2 Breast Cancer Susceptibility Gene", *Cancer Research,* Aug. 1, 1997; 57:3121–3125.

Miki, Y. et al. "A Strong Candidate for the Breast and Ovarian Cancer Susceptibility Gene BRCA1", *Science,* Oct. 7, 1994; 266:66–71.

Monteiro, A.N.A. et al. "Evidence for a transcriptional activation function of BRCA1 C–terminal region", *Proc. Natl. Acad. Sci. USA,* Nov. 1996; 93:13595–13599.

Schaeper, U. et al. "Molecular cloning and characterization of a cellular phosphoprotein that interacts with a conserved C–terminal domain of adenovirus E1A involved in a negative modulation of oncogenic transformation", *Proc. Natl. Acad. Sci. USA,* Nov. 1995; 92:10467–10471.

Schaeper, U. et al. "Interaction between a Cellular Protein That Binds to the C–terminal Region of Adenovirus E1A (CtBP) and a Novel Cellular Protein Is Disrupted by E1A through a Conserved PLDLS Motif", *J. Biol. Chem.,* Apr. 10, 1998; 273(15):8549–8552.

Scully, R. et al. "Dynamic Changes of BRCA1 Subnuclear Location and Phosphorylation State Are Initiated by DNA Damage", *Cell,* Aug. 8, 1997; 90:425–435.

Scully, R. et al. "Association of BRCA1 with Rad51 in Mitotic and Meiotic Cells", *Cell,* Jan. 24, 1997; 88:265–275.

Scully, R. et al. "BRCA1 is a component of the RNA polymerase II holoenzyme", *Proc. Natl. Acad. Sci. USA,* May 1997; 94:5605–5610.

Shao, N. et al. "Induction of apoptosis by the tumor suppressor protein BRCA1", *Oncogene,* 1996; 13:1–7.

Sharan, S.K. et al. "Embryonic lethality and radiation hypersensitivity mediated by Rad51 in mice lacking Brca2", *Nature,* Apr. 1997; 386:804–810.

Shattuck–Eidens, D. et al. "BRCA1 Sequence Analysis in Women at High Risk for Susceptibility Mutations", *JAMA,* Oct. 15, 1997; 278(15):1242–1250.

Shinohara, A., et al. "Rad51 Protein Involved in Repair and Recombination in *S. cerevisiae* Is a RecA–like Protein", *Cell,* May 1, 1992, 69:457–470.

Shinohara, A., et al. "Cloning of human, mouse and fission yeast recombination genes homologous to RAD51 and recA", *Nature Genetics,* Jul. 1993, 4:239–243.

Sobol, H., et al. "Truncation at Conserved Terminal Regions of BRCA1 Protein Is Associated with Highly Proliferating Hereditary Breast Cancers", *Cancer Research,* Jul. 15, 1996; 56:3216–3219.

Sollerbrant, K., et al. "The CtBP binding domain in the adenovirus E1A protein controls CR1–dependent transactivation", *Nucleic Acids Research,* 1996; 24(13):2578–2584.

Somasundaram, K., et al. "Arrest of the cell cycle by the tumour–suppressor BRCA1 requires the CDK–inhibitor $p21^{WAF1/CIP1}$", *Nature,* Sep. 11, 1997; 389:187–190.

Suzuki, A., et al. "Brca2 is required for embryonic cellular proliferation in the mouse", *Genes & Development,* 1997, 11:1242–1252.

Tavtigian, S.V., et al. "The complete BRCA2 gene and mutations in chromosome 13q–linked kindreds", *Nature Genetics,* Mar. 1996; 12:333–337.

Thomas, J.E. et al. "Subcellular Localization and Analysis of Apparent 180–kDa and 220–kDa Proteins of the Breast Cancer Susceptibility Gene, BRCA1", *J. Biol. Chem.,* Nov. 8, 1996; 271(45):28630–28635.

Wilson, C.A., et al. "Differential subcellular localization, expression and biological toxicity of BRCA1 and the splice variant BRCA1–Δ11b", *Oncogene,* 1997; 14:1–16.

Wong, A.K.C., et al. "Characterization of a carboxy–terminal BRCA1 interacting protein", *Oncogene,* Nov. 5, 1998; 17(18):2279–2285.

Wong, A.K.C., et al. "RAD51 Interacts with the Evolutionarily Conserved BRC Motifs in the Human Breast Cancer Susceptibility Gene brca2", *J. Biol. Chem.,* Dec. 19, 1997; 272(51):31941–31944.

Wu, L.C., et al. "Identification of a RING protein that can interact in vivo with the BRCA1 gene product", *Nature Genetics,* Dec. 1996; 14:430–440.

Yu, Xin, et al. "The C–terminal (BRCT) Domains of BRCA1 Interact in Vivo with CtIP, a Protein Implicated in the CtBP Pathway of Transcriptional Repression", *J. Biol. Chem.,* Sep. 25, 1998; 273(39):25388–25392.

SEQUENCE LISTING (1) GENERAL INFORMATION:

(iii) NUMBER OF SEQUENCES: 41

(2) INFORMATION FOR SEQ ID NO: 1:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Primer"

(xi) SEQUENCE DESCRIPTION: SEQ ID NO: 1:

ATGATCTTGT TCACTTCAGA CCCAAGAC                                    28

(2) INFORMATION FOR SEQ ID NO: 2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 2:

TCCTCTACGT CCACGTGAAA GTTTG                                       25

(2) INFORMATION FOR SEQ ID NO: 3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 3:

GCGAAAGAGA AAGCGAGCA GCCG                                         24

(2) INFORMATION FOR SEQ ID NO: 4:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 4:

GAGTGCAAAA TGAAAGCGCC TTATTG                                      26

(2) INFORMATION FOR SEQ ID NO: 5:

(i) SEQUENCE CHARACTERISTICS:
        (A) LENGTH: 2694 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (ix) FEATURE:
    (A) NAME/KEY: CDS
    (B) LOCATION: 1..2691

(xi) SEQUENCE DESCRIPTION: SEQ ID NO: 5:

| | | | | | | | | | | | | | | | | |
|---|---|---|---|---|---|---|---|---|---|---|---|---|---|---|---|---|
| ATG | AAC | ATC | TCG | GGA | AGC | AGC | TGT | GGA | AGC | CCT | AAC | TCT | GCA | GAT | ACA | 48 |
| Met | Asn | Ile | Ser | Gly | Ser | Ser | Cys | Gly | Ser | Pro | Asn | Ser | Ala | Asp | Thr | |
| 1 | | | | 5 | | | | | 10 | | | | | 15 | | |
| TCT | AGT | GAC | TTT | AAG | GAC | CTT | TGG | ACA | AAA | CTA | AAA | GAA | TGT | CAT | GAT | 96 |
| Ser | Ser | Asp | Phe | Lys | Asp | Leu | Trp | Thr | Lys | Leu | Lys | Glu | Cys | His | Asp | |
| | | | 20 | | | | | 25 | | | | | 30 | | | |
| AGA | GAA | GTA | CAA | GGT | TTA | CAA | GTA | AAA | GTA | ACC | AAG | CTA | AAA | CAG | GAA | 144 |
| Arg | Glu | Val | Gln | Gly | Leu | Gln | Val | Lys | Val | Thr | Lys | Leu | Lys | Gln | Glu | |
| | | 35 | | | | | 40 | | | | | 45 | | | | |
| CGA | ATC | TTA | GAT | GCA | CAA | AGA | CTA | GAA | GAA | TTC | TTC | ACC | AAA | AAT | CAA | 192 |
| Arg | Ile | Leu | Asp | Ala | Gln | Arg | Leu | Glu | Glu | Phe | Phe | Thr | Lys | Asn | Gln | |
| | 50 | | | | | 55 | | | | | 60 | | | | | |
| CAG | CTG | AGG | GAA | CAG | CAG | AAA | GTC | CTT | CAT | GAA | ACC | ATT | AAA | GTT | TTA | 240 |
| Gln | Leu | Arg | Glu | Gln | Gln | Lys | Val | Leu | His | Glu | Thr | Ile | Lys | Val | Leu | |
| 65 | | | | | 70 | | | | | 75 | | | | | 80 | |
| GAA | GAT | CGG | TTA | AGA | GCA | GGC | TTA | TGT | GAT | CGC | TGT | GCA | GTA | ACT | GAA | 288 |
| Glu | Asp | Arg | Leu | Arg | Ala | Gly | Leu | Cys | Asp | Arg | Cys | Ala | Val | Thr | Glu | |
| | | | | 85 | | | | | 90 | | | | | 95 | | |
| GAA | CAT | ATG | CGG | AAA | AAA | CAG | CAA | GAG | TTT | GAA | AAT | ATC | CGG | CAG | CAG | 336 |
| Glu | His | Met | Arg | Lys | Lys | Gln | Gln | Glu | Phe | Glu | Asn | Ile | Arg | Gln | Gln | |
| | | | 100 | | | | | 105 | | | | | 110 | | | |
| AAT | CTT | AAA | CTT | ATT | ACA | GAA | CTT | ATG | AAT | GAA | AGG | AAT | ACT | CTA | CAG | 384 |
| Asn | Leu | Lys | Leu | Ile | Thr | Glu | Leu | Met | Asn | Glu | Arg | Asn | Thr | Leu | Gln | |
| | | 115 | | | | | 120 | | | | | 125 | | | | |
| GAA | GAA | AAT | AAA | AAG | CTT | TCT | GAA | CAA | CTC | CAG | CAG | AAA | ATT | GAG | AAT | 432 |
| Glu | Glu | Asn | Lys | Lys | Leu | Ser | Glu | Gln | Leu | Gln | Gln | Lys | Ile | Glu | Asn | |
| | 130 | | | | | 135 | | | | | 140 | | | | | |
| GAT | CAA | CAG | CAT | CAA | GCA | GCT | GAG | CTT | GAA | TGT | GAG | GAA | GAC | GTT | ATT | 480 |
| Asp | Gln | Gln | His | Gln | Ala | Ala | Glu | Leu | Glu | Cys | Glu | Glu | Asp | Val | Ile | |
| 145 | | | | | 150 | | | | | 155 | | | | | 160 | |
| CCA | GAT | TCA | CCG | ATA | ACA | GCC | TTC | TCA | TTT | TCT | GGC | GTT | AAC | CGG | CTA | 528 |
| Pro | Asp | Ser | Pro | Ile | Thr | Ala | Phe | Ser | Phe | Ser | Gly | Val | Asn | Arg | Leu | |
| | | | | 165 | | | | | 170 | | | | | 175 | | |
| CGA | AGA | AAG | GAG | AAC | CCC | CAT | GTC | CGA | TAC | ATA | GAA | CAA | ACA | CAT | ACT | 576 |
| Arg | Arg | Lys | Glu | Asn | Pro | His | Val | Arg | Tyr | Ile | Glu | Gln | Thr | His | Thr | |
| | | | 180 | | | | | 185 | | | | | 190 | | | |
| AAA | TTG | GAG | CAC | TCT | GTG | TGT | GCA | AAT | GAA | ATG | AGA | AAA | GTT | TCC | AAG | 624 |
| Lys | Leu | Glu | His | Ser | Val | Cys | Ala | Asn | Glu | Met | Arg | Lys | Val | Ser | Lys | |
| | | 195 | | | | | 200 | | | | | 205 | | | | |
| TCT | TCA | ACT | CAT | CCA | CAA | CAT | AAT | CCT | AAT | GAA | AAT | GAA | ATT | CTA | GTA | 672 |
| Ser | Ser | Thr | His | Pro | Gln | His | Asn | Pro | Asn | Glu | Asn | Glu | Ile | Leu | Val | |
| | 210 | | | | | 215 | | | | | 220 | | | | | |
| GCT | GAC | ACT | TAT | GAC | CAA | AGT | CAA | TCT | CCA | ATG | GCC | AAA | GCA | CAT | GGA | 720 |
| Ala | Asp | Thr | Tyr | Asp | Gln | Ser | Gln | Ser | Pro | Met | Ala | Lys | Ala | His | Gly | |
| 225 | | | | | 230 | | | | | 235 | | | | | 240 | |
| ACA | AGC | AGC | TAT | ACC | CCT | GAT | AAG | TCA | TCT | TTT | AAT | TTA | GCT | ACA | GTT | 768 |
| Thr | Ser | Ser | Tyr | Thr | Pro | Asp | Lys | Ser | Ser | Phe | Asn | Leu | Ala | Thr | Val | |
| | | | | 245 | | | | | 250 | | | | | 255 | | |
| GTT | GCT | GAA | ACA | CTT | GGA | CTT | GGT | GTT | CAA | GAA | GAA | TCT | GAA | ACT | CAA | 816 |
| Val | Ala | Glu | Thr | Leu | Gly | Leu | Gly | Val | Gln | Glu | Glu | Ser | Glu | Thr | Gln | |
| | | | 260 | | | | | 265 | | | | | 270 | | | |
| GGT | CCC | ATG | AGC | CCC | CTT | GGT | GAT | GAG | CTC | TAC | CAC | TGT | CTG | GAA | GGA | 864 |
| Gly | Pro | Met | Ser | Pro | Leu | Gly | Asp | Glu | Leu | Tyr | His | Cys | Leu | Glu | Gly | |
| | | 275 | | | | | 280 | | | | | 285 | | | | |

```
AAT CAC AAG AAA CAG CCT TTT GAG GAA TCT ACA AGA AAT ACT GAA GAT      912
Asn His Lys Lys Gln Pro Phe Glu Glu Ser Thr Arg Asn Thr Glu Asp
    290                 295                 300

AGT TTA AGA TTT TCA GAT TCT ACT TCA AAG ACT CCT CCT CAA GAA GAA      960
Ser Leu Arg Phe Ser Asp Ser Thr Ser Lys Thr Pro Pro Gln Glu Glu
305                 310                 315                 320

TTA CCT ACT CGA GTG TCA TCT CCT GTA TTT GGA GCT ACC TCT AGT ATC     1008
Leu Pro Thr Arg Val Ser Ser Pro Val Phe Gly Ala Thr Ser Ser Ile
                325                 330                 335

AAA AGT GGT TTA GAT TTG AAT ACA AGT TTG TCC CCT TCT CTT TTA CAG     1056
Lys Ser Gly Leu Asp Leu Asn Thr Ser Leu Ser Pro Ser Leu Leu Gln
            340                 345                 350

CCT GGG AAA AAA AAA CAT CTG AAA ACA CTC CCT TTT AGC AAC ACT TGT     1104
Pro Gly Lys Lys Lys His Leu Lys Thr Leu Pro Phe Ser Asn Thr Cys
        355                 360                 365

ATA TCT AGA TTA GAA AAA ACT AGA TCA AAA TCT GAA GAT AGT GCC CTT     1152
Ile Ser Arg Leu Glu Lys Thr Arg Ser Lys Ser Glu Asp Ser Ala Leu
    370                 375                 380

TTC ACA CAT CAC AGT CTT GGG TCT GAA GTG AAC AAG ATC ATT ATC CAG     1200
Phe Thr His His Ser Leu Gly Ser Glu Val Asn Lys Ile Ile Ile Gln
385                 390                 395                 400

TCA TCT AAT AAA CAG ATA CTT ATA AAT AAA AAT ATA AGT GAA TCC CTA     1248
Ser Ser Asn Lys Gln Ile Leu Ile Asn Lys Asn Ile Ser Glu Ser Leu
                405                 410                 415

GGT GAA CAG AAT AGG ACT GAG TAC GGT AAA GAT TCT AAC ACT GAT AAA     1296
Gly Glu Gln Asn Arg Thr Glu Tyr Gly Lys Asp Ser Asn Thr Asp Lys
            420                 425                 430

CAT TTG GAG CCC CTG AAA TCA TTG GGA GGC CGA ACA TCC AAA AGG AAG     1344
His Leu Glu Pro Leu Lys Ser Leu Gly Gly Arg Thr Ser Lys Arg Lys
        435                 440                 445

AAA ACT GAG GAA GAA AGT GAA CAT GAA GTA AGC TGC CCC CAA GCT TCT     1392
Lys Thr Glu Glu Glu Ser Glu His Glu Val Ser Cys Pro Gln Ala Ser
    450                 455                 460

TTT GAT AAA GAA AAT GCT TTC CCT TTT CCA ATG GAT AAT CAG TTT TCC     1440
Phe Asp Lys Glu Asn Ala Phe Pro Phe Pro Met Asp Asn Gln Phe Ser
465                 470                 475                 480

ATG AAT GGA GAC TGT GTG ATG GAT AAA CCT CTG GAT CTG TCT GAT CGA     1488
Met Asn Gly Asp Cys Val Met Asp Lys Pro Leu Asp Leu Ser Asp Arg
                485                 490                 495

TTT TCA GCT ATT CAG CGT CAA GAG AAA AGC CAA GGA AGT GAG ACT TCT     1536
Phe Ser Ala Ile Gln Arg Gln Glu Lys Ser Gln Gly Ser Glu Thr Ser
            500                 505                 510

AAA AAC AAA TTT AGG CAA GTG ACT CTT TAT GAG GCT TTG AAG ACC ATT     1584
Lys Asn Lys Phe Arg Gln Val Thr Leu Tyr Glu Ala Leu Lys Thr Ile
        515                 520                 525

CCA AAG GGC TTT TCC TCA AGC CGT AAG GCC TCA GAT GGC AAC TGC ACG     1632
Pro Lys Gly Phe Ser Ser Ser Arg Lys Ala Ser Asp Gly Asn Cys Thr
    530                 535                 540

TTG CCC AAA GAT TCC CCA GGG GAG CCC TGT TCA CAG GAA TGC ATC ATC     1680
Leu Pro Lys Asp Ser Pro Gly Glu Pro Cys Ser Gln Glu Cys Ile Ile
545                 550                 555                 560

CTT CAG CCC TTG AAT AAA TGC TCT CCA GAC AAT AAA CCA TCA TTA CAA     1728
Leu Gln Pro Leu Asn Lys Cys Ser Pro Asp Asn Lys Pro Ser Leu Gln
                565                 570                 575

ATA AAA GAA GAA AAT GCT GTC TTT AAA ATT CCT CTA CGT CCA CGT GAA     1776
Ile Lys Glu Glu Asn Ala Val Phe Lys Ile Pro Leu Arg Pro Arg Glu
            580                 585                 590

AGT TTG GAG ACT GAG AAT GTT TTA GAT GAC ATA AAG AGT GCT GGT TCT     1824
Ser Leu Glu Thr Glu Asn Val Leu Asp Asp Ile Lys Ser Ala Gly Ser
        595                 600                 605
```

```
CAT GAG CCA ATA AAA ATA CAA ACC AGG TCA GAC CAT GGA GGA TGT GAA    1872
His Glu Pro Ile Lys Ile Gln Thr Arg Ser Asp His Gly Gly Cys Glu
        610             615                 620

CTT GCA TCA GTT CTT CAG TTA AAT CCA TGT AGA ACT GGT AAA ATA AAG    1920
Leu Ala Ser Val Leu Gln Leu Asn Pro Cys Arg Thr Gly Lys Ile Lys
625             630                 635                 640

TCT CTA CAA AAC AAC CAA GAT GTA TCC TTT GAA AAT ATC CAG TGG AGT    1968
Ser Leu Gln Asn Asn Gln Asp Val Ser Phe Glu Asn Ile Gln Trp Ser
                645                 650                 655

ATA GAT CCG GGA GCA GAC CTT TCT CAG TAT AAA ATG GAT GTT ACT GTA    2016
Ile Asp Pro Gly Ala Asp Leu Ser Gln Tyr Lys Met Asp Val Thr Val
            660                 665                 670

ATA GAT ACA AAG GAT GGC AGT CAG TCA AAA TTA GGA GGA GAG ACA GTG    2064
Ile Asp Thr Lys Asp Gly Ser Gln Ser Lys Leu Gly Gly Glu Thr Val
        675                 680                 685

GAC ATG GAC TGT ACA TTG GTT AGT GAA ACC GTT CTC TTA AAA ATG AAG    2112
Asp Met Asp Cys Thr Leu Val Ser Glu Thr Val Leu Leu Lys Met Lys
690                 695                 700

AAG CAA GAG CAG AAG GGA GAA AAA AGT TCA AAT GAA GAA AGA AAA ATG    2160
Lys Gln Glu Gln Lys Gly Glu Lys Ser Ser Asn Glu Glu Arg Lys Met
705                 710                 715                 720

AAT GAT AGC TTG GAA GAT ATG TTT GAT CGG ACA ACA CAT GAA GAG TAT    2208
Asn Asp Ser Leu Glu Asp Met Phe Asp Arg Thr Thr His Glu Glu Tyr
            725                 730                 735

GAA TCC TGT TTG GCA GAC AGT TTC TCC CAA GCA GCA GAT GAA GAG GAG    2256
Glu Ser Cys Leu Ala Asp Ser Phe Ser Gln Ala Ala Asp Glu Glu Glu
            740                 745                 750

GAA TTG TCT ACT GCC ACA AAG AAA CTA CAC ACT CAT GGT GAT AAA CAA    2304
Glu Leu Ser Thr Ala Thr Lys Lys Leu His Thr His Gly Asp Lys Gln
        755                 760                 765

GAC AAA GTC AAG CAG AAA GCG TTT GTG GAG CCG TAT TTT AAA GGT GAT    2352
Asp Lys Val Lys Gln Lys Ala Phe Val Glu Pro Tyr Phe Lys Gly Asp
770                 775                 780

GAA AGA GAG ACT AGC TTG CAA AAT TTT CCT CAT ATT GAG GTG GTT CGG    2400
Glu Arg Glu Thr Ser Leu Gln Asn Phe Pro His Ile Glu Val Val Arg
785                 790                 795                 800

AAA AAA GAG GAG AGA AGA AAA CTG CTT GGG CAC ACG TGT AAG GAA TGT    2448
Lys Lys Glu Glu Arg Arg Lys Leu Leu Gly His Thr Cys Lys Glu Cys
            805                 810                 815

GAA ATT TAT TAT GCA GAT ATG CCA GCA GAA GAA AGA GAA AAG AAA TTG    2496
Glu Ile Tyr Tyr Ala Asp Met Pro Ala Glu Glu Arg Glu Lys Lys Leu
            820                 825                 830

GCT TCC TGC TCA AGA CAC CGA TTC CGC TAC ATT CCA CCC AAC ACA CCA    2544
Ala Ser Cys Ser Arg His Arg Phe Arg Tyr Ile Pro Pro Asn Thr Pro
        835                 840                 845

GAG AAT TTT TGG GAA GTT GGT TTT CCT TCC ACT CAG ACT TGT ATG GAA    2592
Glu Asn Phe Trp Glu Val Gly Phe Pro Ser Thr Gln Thr Cys Met Glu
850                 855                 860

AGA GGT TAT ATT AAG GAA GAT CTT GAT CCT TGT CCT CGT CCA AAA AGA    2640
Arg Gly Tyr Ile Lys Glu Asp Leu Asp Pro Cys Pro Arg Pro Lys Arg
865                 870                 875                 880

CGT CAG CCT TAC AAC GCA ATA TTT TCT CCA AAA GGC AAG GAG CAG AAG    2688
Arg Gln Pro Tyr Asn Ala Ile Phe Ser Pro Lys Gly Lys Glu Gln Lys
            885                 890                 895

ACA TAG                                                             2694
Thr
```

(2) INFORMATION FOR SEQ ID NO: 6:

-continued (i) SEQUENCE CHARACTERISTICS:
(A) LENGTH: 897 amino acids
(B) TYPE: amino acid
(D) TOPOLOGY: linear (ii) MOLECULE TYPE: protein (xi) SEQUENCE DESCRIPTION: SEQ ID NO: 6:

```
Met Asn Ile Ser Gly Ser Ser Cys Gly Ser Pro Asn Ser Ala Asp Thr
  1               5                  10                  15

Ser Ser Asp Phe Lys Asp Leu Trp Thr Lys Leu Lys Glu Cys His Asp
                 20                  25                  30

Arg Glu Val Gln Gly Leu Gln Val Lys Val Thr Lys Leu Lys Gln Glu
             35                  40                  45

Arg Ile Leu Asp Ala Gln Arg Leu Glu Glu Phe Phe Thr Lys Asn Gln
         50                  55                  60

Gln Leu Arg Glu Gln Gln Lys Val Leu His Glu Thr Ile Lys Val Leu
 65                  70                  75                  80

Glu Asp Arg Leu Arg Ala Gly Leu Cys Asp Arg Cys Ala Val Thr Glu
                 85                  90                  95

Glu His Met Arg Lys Gln Gln Glu Phe Glu Asn Ile Arg Gln Gln
                100                 105                 110

Asn Leu Lys Leu Ile Thr Glu Leu Met Asn Glu Arg Asn Thr Leu Gln
            115                 120                 125

Glu Glu Asn Lys Lys Leu Ser Glu Gln Leu Gln Gln Lys Ile Glu Asn
130                 135                 140

Asp Gln Gln His Gln Ala Ala Glu Leu Glu Cys Glu Glu Asp Val Ile
145                 150                 155                 160

Pro Asp Ser Pro Ile Thr Ala Phe Ser Phe Ser Gly Val Asn Arg Leu
                165                 170                 175

Arg Arg Lys Glu Asn Pro His Val Arg Tyr Ile Glu Gln Thr His Thr
            180                 185                 190

Lys Leu Glu His Ser Val Cys Ala Asn Glu Met Arg Lys Val Ser Lys
            195                 200                 205

Ser Ser Thr His Pro Gln His Asn Pro Asn Glu Asn Glu Ile Leu Val
210                 215                 220

Ala Asp Thr Tyr Asp Gln Ser Gln Ser Pro Met Ala Lys Ala His Gly
225                 230                 235                 240

Thr Ser Ser Tyr Thr Pro Asp Lys Ser Ser Phe Asn Leu Ala Thr Val
                245                 250                 255

Val Ala Glu Thr Leu Gly Leu Gly Val Gln Glu Glu Ser Glu Thr Gln
            260                 265                 270

Gly Pro Met Ser Pro Leu Gly Asp Glu Leu Tyr His Cys Leu Glu Gly
            275                 280                 285

Asn His Lys Lys Gln Pro Phe Glu Glu Ser Thr Arg Asn Thr Glu Asp
290                 295                 300

Ser Leu Arg Phe Ser Asp Ser Thr Ser Lys Thr Pro Gln Glu Glu
305                 310                 315                 320

Leu Pro Thr Arg Val Ser Ser Pro Val Phe Gly Ala Thr Ser Ser Ile
                325                 330                 335

Lys Ser Gly Leu Asp Leu Asn Thr Ser Leu Ser Pro Ser Leu Leu Gln
            340                 345                 350

Pro Gly Lys Lys Lys His Leu Lys Thr Leu Pro Phe Ser Asn Thr Cys
            355                 360                 365

Ile Ser Arg Leu Glu Lys Thr Arg Ser Lys Ser Glu Asp Ser Ala Leu
```

-continued

```
            370                 375                 380
Phe Thr His His Ser Leu Gly Ser Glu Val Asn Lys Ile Ile Ile Gln
385                 390                 395                 400

Ser Ser Asn Lys Gln Ile Leu Ile Asn Lys Asn Ile Ser Glu Ser Leu
                405                 410                 415

Gly Glu Gln Asn Arg Thr Glu Tyr Gly Lys Asp Ser Asn Thr Asp Lys
                420                 425                 430

His Leu Glu Pro Leu Lys Ser Leu Gly Gly Arg Thr Ser Lys Arg Lys
                435                 440                 445

Lys Thr Glu Glu Ser Glu His Glu Val Ser Cys Pro Gln Ala Ser
                450                 455                 460

Phe Asp Lys Glu Asn Ala Phe Pro Phe Pro Met Asp Asn Gln Phe Ser
465                 470                 475                 480

Met Asn Gly Asp Cys Val Met Asp Lys Pro Leu Asp Leu Ser Asp Arg
                485                 490                 495

Phe Ser Ala Ile Gln Arg Gln Glu Lys Ser Gln Gly Ser Glu Thr Ser
                500                 505                 510

Lys Asn Lys Phe Arg Gln Val Thr Leu Tyr Glu Ala Leu Lys Thr Ile
                515                 520                 525

Pro Lys Gly Phe Ser Ser Arg Lys Ala Ser Asp Gly Asn Cys Thr
                530                 535                 540

Leu Pro Lys Asp Ser Pro Gly Glu Pro Cys Ser Gln Glu Cys Ile Ile
545                 550                 555                 560

Leu Gln Pro Leu Asn Lys Cys Ser Pro Asp Asn Lys Pro Ser Leu Gln
                565                 570                 575

Ile Lys Glu Glu Asn Ala Val Phe Lys Ile Pro Leu Arg Pro Arg Glu
                580                 585                 590

Ser Leu Glu Thr Glu Asn Val Leu Asp Asp Ile Lys Ser Ala Gly Ser
                595                 600                 605

His Glu Pro Ile Lys Ile Gln Thr Arg Ser Asp His Gly Gly Cys Glu
                610                 615                 620

Leu Ala Ser Val Leu Gln Leu Asn Pro Cys Arg Thr Gly Lys Ile Lys
625                 630                 635                 640

Ser Leu Gln Asn Asn Gln Asp Val Ser Phe Glu Asn Ile Gln Trp Ser
                645                 650                 655

Ile Asp Pro Gly Ala Asp Leu Ser Gln Tyr Lys Met Asp Val Thr Val
                660                 665                 670

Ile Asp Thr Lys Asp Gly Ser Gln Ser Lys Leu Gly Gly Glu Thr Val
                675                 680                 685

Asp Met Asp Cys Thr Leu Val Ser Glu Thr Val Leu Leu Lys Met Lys
690                 695                 700

Lys Gln Glu Gln Lys Gly Glu Lys Ser Ser Asn Glu Glu Arg Lys Met
705                 710                 715                 720

Asn Asp Ser Leu Glu Asp Met Phe Asp Arg Thr Thr His Glu Glu Tyr
                725                 730                 735

Glu Ser Cys Leu Ala Asp Ser Phe Ser Gln Ala Ala Asp Glu Glu
                740                 745                 750

Glu Leu Ser Thr Ala Thr Lys Lys Leu His Thr His Gly Asp Lys Gln
                755                 760                 765

Asp Lys Val Lys Gln Lys Ala Phe Val Glu Pro Tyr Phe Lys Gly Asp
                770                 775                 780

Glu Arg Glu Thr Ser Leu Gln Asn Phe Pro His Ile Glu Val Val Arg
785                 790                 795                 800
```

```
Lys Lys Glu Glu Arg Arg Lys Leu Leu Gly His Thr Cys Lys Glu Cys
            805                 810                 815

Glu Ile Tyr Tyr Ala Asp Met Pro Ala Glu Glu Arg Glu Lys Lys Leu
            820                 825                 830

Ala Ser Cys Ser Arg His Arg Phe Arg Tyr Ile Pro Pro Asn Thr Pro
            835                 840                 845

Glu Asn Phe Trp Glu Val Gly Phe Pro Ser Thr Gln Thr Cys Met Glu
        850                 855                 860

Arg Gly Tyr Ile Lys Glu Asp Leu Asp Pro Cys Pro Arg Pro Lys Arg
865                 870                 875                 880

Arg Gln Pro Tyr Asn Ala Ile Phe Ser Pro Lys Gly Lys Glu Gln Lys
            885                 890                 895

Thr
```

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 7:

GGCGGTATTT GACCTGTCCA                                         20

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 8:

CTTGCTTAAT ATGCTCCACA C                                       21

(2) INFORMATION FOR SEQ ID NO: 9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 9:

CACAGCCTCA GAAAGTGCTC G                                       21

(2) INFORMATION FOR SEQ ID NO: 10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "Primer"

(xi) SEQUENCE DESCRIPTION: SEQ ID NO: 10:

AAGTGTTGCT AAAAGGGAGT G                                              21

(2) INFORMATION FOR SEQ ID NO: 11:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 11:

GTTTTCCCAG TCACGACGGA GGCGGTATTT GACCTGTCC                            39

(2) INFORMATION FOR SEQ ID NO: 12:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 12:

AGGAAACAGC TATGACCATC TTCAGTTACT GCACAGCGAT                           40

(2) INFORMATION FOR SEQ ID NO: 13:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 13:

GTTTTCCCAG TCACGACGAA AATCAACAGC TGAGGGAACA                           40

(2) INFORMATION FOR SEQ ID NO: 14:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 14:

AGGAAACAGC TATGACCATG TTCTCCTTTC TTCGTAGCCG                           40

(2) INFORMATION FOR SEQ ID NO: 15:

(i) SEQUENCE CHARACTERISTICS:
        (A) LENGTH: 39 base pairs
        (B) TYPE: nucleic acid
        (C) STRANDEDNESS: single
        (D) TOPOLOGY: linear

```
        (ii) MOLECULE TYPE: other nucleic acid
             (A) DESCRIPTION: /desc = "Primer"

(xi) SEQUENCE DESCRIPTION: SEQ ID NO: 15:

GTTTTCCCAG TCACGACGCA CCGATAACAG CCTTCTCAT                              39

(2) INFORMATION FOR SEQ ID NO: 16:

(i) SEQUENCE CHARACTERISTICS:
             (A) LENGTH: 40 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "Primer"

(xi) SEQUENCE DESCRIPTION: SEQ ID NO: 16:

AGGAAACAGC TATGACCATT GGGACCTTGA GTTTCAGATT                             40

(2) INFORMATION FOR SEQ ID NO: 17:

(i) SEQUENCE CHARACTERISTICS:
             (A) LENGTH: 40 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "Primer"

(xi) SEQUENCE DESCRIPTION: SEQ ID NO: 17:

GTTTTCCCAG TCACGACGAC CCCTGATAAG TCATCTTTTA                             40

(2) INFORMATION FOR SEQ ID NO: 18:

(i) SEQUENCE CHARACTERISTICS:
             (A) LENGTH: 41 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "Primer"

(xi) SEQUENCE DESCRIPTION: SEQ ID NO: 18:

AGGAAACAGC TATGACCATG GGACAAACTT GTATTCAAAT C                           41

(2) INFORMATION FOR SEQ ID NO: 19:

(i) SEQUENCE CHARACTERISTICS:
             (A) LENGTH: 22 base pairs
             (B) TYPE: nucleic acid
             (C) STRANDEDNESS: single
             (D) TOPOLOGY: linear (ii) MOLECULE TYPE: other nucleic acid
             (A) DESCRIPTION: /desc = "Primer"

(xi) SEQUENCE DESCRIPTION: SEQ ID NO: 19:

AGATTCTACT TCAAAGACTC CT                                                22

(2) INFORMATION FOR SEQ ID NO: 20:

(i) SEQUENCE CHARACTERISTICS:
             (A) LENGTH: 22 base pairs
             (B) TYPE: nucleic acid
             (C) STRANDEDNESS: single
             (D) TOPOLOGY: linear
```

(ii) MOLECULE TYPE: other nucleic acid
            (A) DESCRIPTION: /desc = "Primer"

(xi) SEQUENCE DESCRIPTION: SEQ ID NO: 20:

TTATCACCAT GAGTGTGTAG TT                                                22

(2) INFORMATION FOR SEQ ID NO: 21:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 21:

GTTTTCCCAG TCACGACGCG AGTGTCATCT CCTGTATTT                              39

(2) INFORMATION FOR SEQ ID NO: 22:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 22:

AGGAAACAGC TATGACCATG GCAGCTTACT TCATGTTCAC                             40

(2) INFORMATION FOR SEQ ID NO: 23:

(i) SEQUENCE CHARACTERISTICS:
            (A) LENGTH: 39 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 23:

GTTTTCCCAG TCACGACGGA TAAACATTTG GAGCCCCTG                              39

(2) INFORMATION FOR SEQ ID NO: 24:

(i) SEQUENCE CHARACTERISTICS:
            (A) LENGTH: 40 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "Primer"

(xi) SEQUENCE DESCRIPTION: SEQ ID NO: 24:

AGGAAACAGC TATGACCATA ACGTGCAGTT GCCATCTGAG                             40

(2) INFORMATION FOR SEQ ID NO: 25:

(i) SEQUENCE CHARACTERISTICS:
            (A) LENGTH: 39 base pairs
            (B) TYPE: nucleic acid
            (C) STRANDEDNESS: single (D) TOPOLOGY: linear (ii) MOLECULE TYPE: other nucleic acid
         (A) DESCRIPTION: /desc = "Primer"

(xi) SEQUENCE DESCRIPTION: SEQ ID NO: 25:

GTTTTCCCAG TCACGACGAG GCAAGTGACT CTTTATGAG                    39

(2) INFORMATION FOR SEQ ID NO: 26:

(i) SEQUENCE CHARACTERISTICS:
         (A) LENGTH: 41 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer"

(xi) SEQUENCE DESCRIPTION: SEQ ID NO: 26:

AGGAAACAGC TATGACCATA TCTTGGTTGT TTTGTAGAGA C                 41

(2) INFORMATION FOR SEQ ID NO: 27:

(i) SEQUENCE CHARACTERISTICS:
         (A) LENGTH: 40 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer"

(xi) SEQUENCE DESCRIPTION: SEQ ID NO: 27:

GTTTTCCCAG TCACGACGAA AAATACAAAC CAGGTCAGAC                   40

(2) INFORMATION FOR SEQ ID NO: 28:

(i) SEQUENCE CHARACTERISTICS:
         (A) LENGTH: 40 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer"

(xi) SEQUENCE DESCRIPTION: SEQ ID NO: 28:

AGGAAACAGC TATGACCATT CTGCCAAACA GGATTCATAC                   40

(2) INFORMATION FOR SEQ ID NO: 29:

(i) SEQUENCE CHARACTERISTICS:
         (A) LENGTH: 23 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Primer"

(xi) SEQUENCE DESCRIPTION: SEQ ID NO: 29:

TCATTTTCTG GCGTTAACCG GCT                                    23

(2) INFORMATION FOR SEQ ID NO: 30:

(i) SEQUENCE CHARACTERISTICS:
         (A) LENGTH: 24 base pairs
         (B) TYPE: nucleic acid

```
           (C) STRANDEDNESS: single
           (D) TOPOLOGY: linear (ii) MOLECULE TYPE: other nucleic acid
           (A) DESCRIPTION: /desc = "Primer"

(xi) SEQUENCE DESCRIPTION: SEQ ID NO: 30:

GTCTGGAGAG CATTTATTCA AGGG                                              24

(2) INFORMATION FOR SEQ ID NO: 31:

(i) SEQUENCE CHARACTERISTICS:
           (A) LENGTH: 42 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Primer"

(xi) SEQUENCE DESCRIPTION: SEQ ID NO: 31:

GTTTTCCCAG TCACGACGGG AAGGAAATCA CAAGAAACAG CC                          42

(2) INFORMATION FOR SEQ ID NO: 32:

(i) SEQUENCE CHARACTERISTICS:
           (A) LENGTH: 43 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Primer"

(xi) SEQUENCE DESCRIPTION: SEQ ID NO: 32:

AGGAAACAGC TATGACCATG GGCACTATCT TCAGATTTTG ATC                         43

(2) INFORMATION FOR SEQ ID NO: 33:

(i) SEQUENCE CHARACTERISTICS:
           (A) LENGTH: 40 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Primer"

(xi) SEQUENCE DESCRIPTION: SEQ ID NO: 33:

GTTTTCCCAG TCACGACGTC AAAGACTCCT CCTCAAGAAG                              40

(2) INFORMATION FOR SEQ ID NO: 34:

(i) SEQUENCE CHARACTERISTICS:
           (A) LENGTH: 43 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = "Primer"

(xi) SEQUENCE DESCRIPTION: SEQ ID NO: 34:

AGGAAACAGC TATGACCATG ATGACTGGAT AATGATCTTG TTC                         43

(2) INFORMATION FOR SEQ ID NO: 35:

(i) SEQUENCE CHARACTERISTICS:
           (A) LENGTH: 22 base pairs
```

(B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 35:

AAATGAAGAA GCAAGAGCAG AA                                                22

(2) INFORMATION FOR SEQ ID NO: 36:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 36:

AGTTAGAGTG CAAAATGAAA GC                                                22

(2) INFORMATION FOR SEQ ID NO: 37:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 37:

GTTTTCCCAG TCACGACGGC AGAAGGGAGA AAAAAGTTC                              39

(2) INFORMATION FOR SEQ ID NO: 38:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 38:

AGGAAACAGC TATGACCATT GTCTTGAGCA GGAAGCCAAT                             40

(2) INFORMATION FOR SEQ ID NO: 39:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 39:

GTTTTCCCAG TCACGACGAG AAGAAAACTG CTTGGGCACA                             40

(2) INFORMATION FOR SEQ ID NO: 40:

(i) SEQUENCE CHARACTERISTICS:

```
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(xi) SEQUENCE DESCRIPTION: SEQ ID NO: 40:

AGGAAACAGC TATGACCATA AACTGTCCTT CATCCTTCTG T                    41

(2) INFORMATION FOR SEQ ID NO: 41:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO: 41:

Asn Ile Ser Gly
```

CARBOXY-TERMINAL BRCA1 INTERACTING PROTEIN

CROSS REFERENCE TO RELATED APPLICATIONS

This is a divisional of Ser. No. 08/975,703, filed Nov. 21, 1997, which issued as U.S. Pat. No. 6,030,832 on Feb. 29, 2000, which is incorporated herein by reference.

BACKGROUND OF THE INVENTION

BRCA1 was the first familial breast and ovarian cancer gene discovered and accounts for approximately 5% of all breast cancer cases (Miki et al., 1994; Cannon-Albright et al., 1996). Currently the mechanisms of tumor suppression by BRCA1 are not well understood. It is plausible that the BRCA1 activities are either regulated or mediated by interactions with other cellular proteins. The disruption of these protein—protein interactions by deleterious mutations in BRCA1 could be one significant step in tumorigenesis. A number of BRCA1 interacting proteins have recently been identified. BARD 1 is a novel protein that binds to the RING finger near the N-terminus of BRCA1 (Wu et al., 1996). Its biological function has not yet been defined, though it is thought to play a role in DNA replication checkpoint control (Scully et al., 1997a; Jin et al., 1997). Certain germline mutations in BRCA1 have been reported to disrupt the interaction with BARD1. Importin-α is a component of the nuclear localization signal (NLS) receptor complex that is believed to associate with the BRCA1 protein (Chen et al., 1996a). It has been proposed that an aberration in the subcellular localization of the BRCA1 protein in breast tumor cells may be a possible mechanism by which the BRCA1 tumor suppressor function is perturbed (Chen et al., 1995). However, questions have been raised about the accuracy of the localization data since conflicting results have been reported by different groups (Thomas et al., 1996; Wilson et al., 1997). RAD51, a homolog to the *E. coli* Rec A protein which is involved in the repair of double-strand DNA breaks, is known to interact with BRCA1 and BRCA2, the second familial breast cancer gene (Shinohara et al., 1992; Tavtigian et al., 1996; Scully et al., 1997b; Sharan et al., 1997). In BRCA2, the sites of RAD51 interaction have been fine mapped to the eight evolutionarily conserved BRC motifs in the internal region of the protein (Wong et al., 1997). The interaction of both breast cancer susceptibility gene products with RAD51 suggests that BRCA1 and BRCA2 participate in the maintenance of genome integrity.

BRCA1 appears to be a multifunctional protein. In addition to a possible role in DNA repair, it has been implicated in the control of cell cycle and cell proliferation (Hakem et al., 1996; Somasundaram et al., 1997) and regulation of transcription (Chapman and Verma, 1996; Monteiro et al., 1996). Scully et al. have shown that BRCA1 is a component of the transcriptionally active RNA polymerase II holoenzyme complex (Scully et al., 1997c). When the carboxy-terminal region of BRCA1 is fused to a heterologous DNA binding domain, transcriptional activation function is observed (Chapman and Verma, 1996; Monteiro et al., 1996). More specifically, BRCA1 can transactivate the expression of cyclin-dependent kinase inhibitor p21 in tissue culture cells resulting in cell cycle arrest at S-phase (Somasundaram et al., 1997). This observation seems to contradict the observation that in knock-out mice p21 overexpression is correlated with the loss of BRCA1 function (Hakem et al., 1996). Some germline mutations at the carboxy-terminal region of BRCA1 are known to abolish the transcriptional activation function (Chapman and Verma, 1996; Monteiro et al., 1996). Yeast two hybrid searches using the carboxy-terminal segment as "bait" to identify interacting proteins that could further our understanding of BRCA1 and the pathway in which it is involved have been conducted and the results are presented here. It is shown that a protein named B112 (or CtIP) is a specific BRCA1 interacting protein. Moreover, the deletion of the last 11 amino acid residues at the carboxy-terminus of BRCA1 by the previously identified 1853ter familial insertion mutation abolishes this protein—protein interaction (Shattuck-Eidens et al., 1995).

The publications and other materials used herein to illuminate the background of the invention or provide additional details respecting the practice, are incorporated by reference, and for convenience are respectively grouped in the appended List of References.

SUMMARY OF THE INVENTION

Sequence conservation at the C-terminal region of the BRCA1 protein among mammalian species suggests some functional significance for that region. Using the yeast two-hybrid and in vitro biochemical assays, it has been found that the partial protein clone B112, which encodes part of the protein known as CtIP (GenBank Accession No. U72066), interacts specifically with a segment of human BRCA1 protein from residues 1602 to 1863. A germline nonsense mutation, 1853ter, that removes the carboxy-terminal 11 amino acids of BRCA1, abolishes not only the transcription activation function of BRCA1, but also binding of BRCA1 to CtIP. The screening of a panel of tumor cell lines has resulted in the identification of a number of missense variants, including a nonconserved lysine to glutamic acid change in the CtIP sequence. Taken together, these results indicate that CtIP and BRCA1 participate in a common biochemical pathway and that the interaction between BRCA1 and CtIP is required for the tumor suppressor activity of BRCA1.

DETAILED DESCRIPTION OF THE INVENTION

Figure 1A:
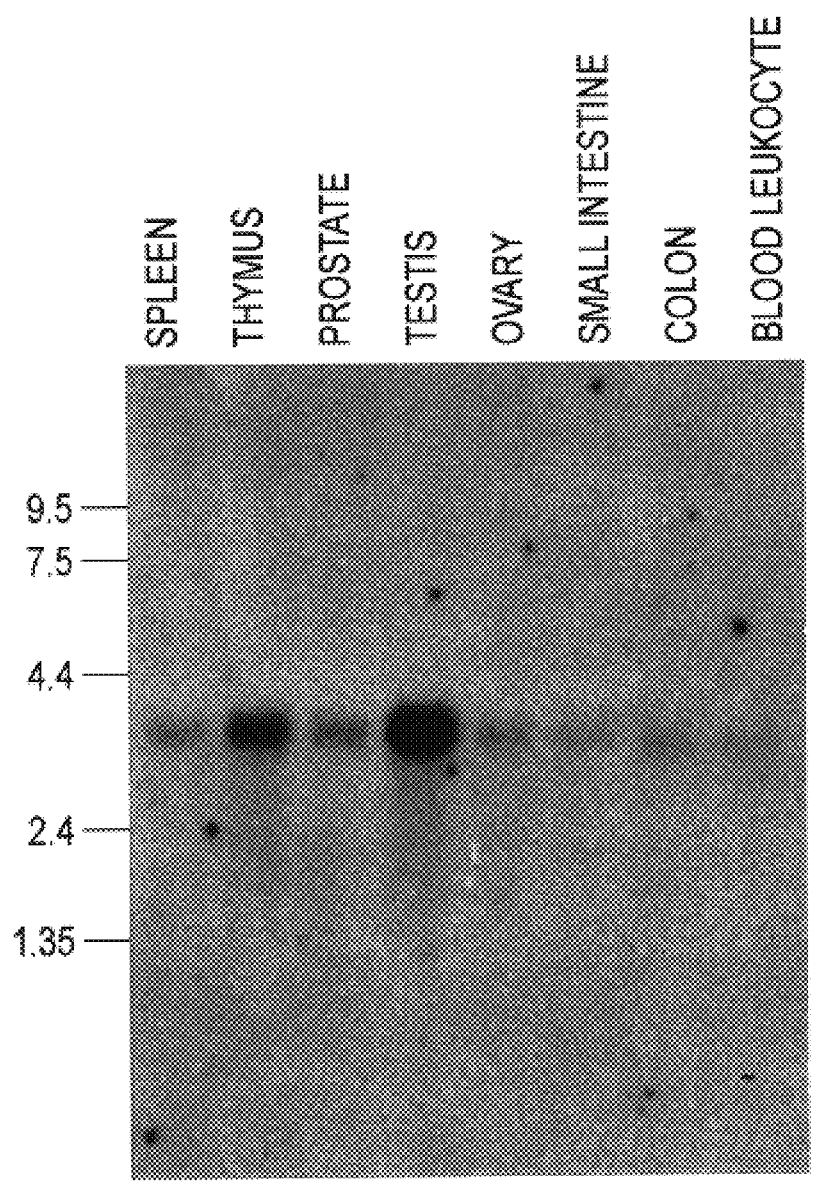
FIGS. 1A–B. Northern analysis of B112 (CtIP). (A) Multi-tissue Northern blot probed with $^{32}$P-labeled B112. (B) The blot in (A) was stripped and reprobed with G3PDH.

BRCA1 was the first familial breast and ovarian cancer gene discovered (Miki et al., 1994). It accounts for approximately 5% of all breast cancer cases (Cannon-Albright et al., 1996). The mechanism by which BRCA1 exerts its tumor suppression is not well understood. Nevertheless, an understanding of the normal physiological function of the BRCA1 protein is emerging. It is believed to play a role in DNA repair through the RAD51 pathway (Sharan et al., 1997; Wong et al., 1997), in the regulation of cell cycle (Somasundaram et al., 1997) and in apoptosis (Shao et al., 1996). BRCA1 is a phosphoprotein that is expressed in a cell cycle dependent manner (Chen et al., 1996b) and changes in its phosphorylation state are induced by DNA damages (Scully et al., 1997a). Alteration of the G2-M cell cycle control in nontumorigenic human breast epithelial cells has recently been demonstrated when the carboxy-terminal segment of BRCA1 was over-expressed (Larson et al., 1997). This perturbation could be due to hyperactivity in the BRCA1 transcription activation function. Since it has been reported that BRCA1 can activate the expression of the cell cycle control gene, p21 (Somasundaram et al., 1997), it may be possible that BRCA1 could also regulate a number of as yet unidentified cell cycle related genes, particularly those that control the G2-M transition phase. It is interesting to point out that the BRCA1 mutation, 1853ter, affects not only the transcription activation function, but also the binding to CtIP. This loss of interaction between the two proteins could be interpreted as a means by which CtIP modulates the transcriptional activity of BRCA1. The DNA repair protein RAD51 is also a component of the RNA polymerase holoenzyme complex (Maldonado et al., 1996). Another hypothetical scenario is that CtIP may serve to coordinate the activities of DNA repair and transcription. This is consistent with its high level of expression in testis and thymus where the repair of double stranded breaks are expected to be frequent.

It is shown here that BRCA1 binds to a protein named CtIP. This is shown by a combination of a yeast two-hybrid assay and an in vitro biochemical assay. It is of interest to point out that the mutation 1853ter, which results in a BRCA1 protein lacking the C-terminal 11 amino acid residues and which is commonly found in patients with familial breast cancer, affects not only the transcription activation function of BRCA1, but also the binding of BRCA1 to CtIP. A role for CtIP may be to modulate the transcription activity of BRCA1. The BRCA1 C-terminal region contains BRCT modules that are found in at least twenty three other proteins, many of which are involved in DNA repair (Koonin et al., 1996; Callebaut and Mornon, 1997). The 11 amino acid deletion in the mutant 1853ter removes the 3' portion of the BRCT consensus sequence, thus indicating that CtIP may bind to other proteins through this motif. The DNA repair protein RAD51 and BRCA1 are components of the RNA polymerase holoenzyme complex, and CtIP may serve to coordinate the activities of DNA repair and transcription.

The clone used in the studies of the present invention is named B112. It is very similar with, but not identical to, the sequence of CtIP reported as Accession No. U72066 in GenBank. A search of the GenBank database with the B112 (CtIP) sequence did not reveal any significant homology to previously identified genes. Based on Northern analysis, CtIP expression is similar to that of human BRCA1, BRCA2 and mouse RAD51, with a high level of RNA expression in testis and thymus (Mild et al., 1994; Tavtigian et al., 1996; Shinohara et al., 1993), This correlation in tissue expression pattern suggests that CtIP may perform a common function in the BRCA1 and BRCA2 pathways. Although a number of other BRCA1 interactions have been identified, CtIP is the only protein known to bind to the BRCA1 carboxy-terminus. There are several lines of evidence supporting the idea that this BRCA1 domain is functionally significant. For example, the carboxy-terminal region of BRCA1 is highly conserved among mammalian species that have been sequenced (McAllister et al., 1997). It contains the BRCT motif which is found in at least 23 other proteins, some of which are involved in DNA repair (Koonin et al., 1996; Callebaut and Mornon, 1997). Many of the familial BRCA1 mutations are truncation mutations that are predicted to eliminate the carboxy-terminus. A recent correlation study has shown that truncation mutations at the conserved carboxy-terminal region of BRCA1 are associated with highly proliferating hereditary breast cancer (Sobol et al., 1996). As demonstrated in the yeast two-hybrid and in vitro biochemical assays disclosed herein, the binding of CtIP to BRCA1 is disrupted by the familial mutation 1853ter at the carboxy-terminus. The high proliferation cancer rate may be related to defects caused by the loss of CtIP-BRCA1 interaction.

As indicated in its GenBank entry (Accession No. U72066), CtIP was originally identified supposedly by interaction with the cellular protein CtBP, which has previously been shown to bind to the carboxy-terminal domain of the adenovirus types 2 and 5 E1A proteins (Schaeper et al., 1995; Sollerbrant et al., 1996). This region of the E1A protein has been shown to modulate in vitro transformation efficiency (Schaeper et al., 1995). The binding of CtIP to CtBP would link E1A to the BRCA1 pathway. Confirmation of these potentially interesting protein—protein interactions are needed as they will provide useful information on the mechanism of action of BRCA1.

If CtIP is a key protein that is involved in tumor suppression activity in the BRCA1 pathway, its corresponding gene is predicted to be mutated. To test this hypothesis, a panel of cDNA samples from 92 tumor cell lines of different cancer types was used as a source for mutation screening. Several missense variants in the coding region of CtIP from pancreas, lung, colon and ovarian cell lines were identified, but it appears that the mutation frequency in this gene is low. One of the base changes involves the conversion of a lysine to glutamic acid, which is a non-conserved substitution. This change in the BxPC3 cell line is accompanied with an apparent loss of heterozygosity at the same locus. Therefore, the CtIP gene itself is a potential tumor suppressor candidate. It may be worthwhile to pursue further the mutation screening of CtIP in primary tumor samples.

The present invention is directed to the determination that the gene CtIP binds to the C-terminal region of BRCA1 and is involved in a common pathway with BRCA1 which is a known tumor suppressor. Molecular variants of CtIP have been found and some of these are involved in the pathogenesis of cancer. More specifically, the present invention relates to mutations in the CtIP gene and their use in the diagnosis of cancer. The present invention is further directed to methods of screening humans for the presence of CtIP gene variants which cause cancer. Since such variants can now be detected earlier, i.e., before symptoms appear, and more definitively, better treatment options will be available in those individuals identified as having harmful mutations in CtIP.

The present invention provides methods of screening the CtIP gene to identify mutations. Such methods may further comprise the step of amplifying a portion of the CtIP gene, and may further include a step of providing a set of polynucleotides which are primers for amplification of said portion of the CtIP gene. The method is useful for identifying mutations for use in either diagnosis of cancer or prognosis of cancer.

Finally, the present invention is directed to a method for screening drug candidates to identify drugs useful for treating or preventing cancer. Drug screening is performed by expressing mutant CtIP and assaying the effect of a drug candidate on the binding of CtIP with BRCA1. Similarly, one can test the effect of a drug candidate on the binding of wild-type CtIP with a mutant BRCA1. Such assays can be performed in vitro or in vivo, such as in oocytes, mammalian cells or transgenic animals. Other assays may test the ability of a drug, wherein the drug may be, e.g., a peptide, to replace the activity of CtIP such that the drug plus BRCA1 will work in concert similar to the normal wild-type interactions of CtIP and BRCA1. Again, similar assays may be performed to screen for drugs which replace a mutant BRCA1 and will bind to wild-type CtIP to replace the BRCA1 function which is lacking as a result of a mutated BRCA1.

According to the diagnostic and prognostic method of the present invention, alteration of the wild-type CtIP gene is detected. In addition, the method can be performed by detecting the wild-type CtIP gene and confirming the lack of a cause of cancer as a result of this locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues and are not inherited in the germline. Germline mutations can be found in any of a body's tissues and are inherited. Point mutational events may occur in regulatory regions, such as in the promoter of the gene, leading to loss or diminution of expression of the mRNA. Point mutations may also abolish proper RNA processing, leading to loss of expression of the CtIP gene product, or to a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis, hybridization using nucleic acid modified with gold nanoparticles and PCR-SSCP, as discussed in detail further below. Also useful is the recently developed technique of DNA microchip technology.

The presence of cancer due to a germline mutation at this locus may be ascertained by testing any tissue of a human for mutations of the CtIP gene. For example, a person who has inherited a germline CtIP mutation would be prone to develop cancer. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the CtIP gene. Alteration of a wild-type CtIP allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of cancer cases. Southern blots displaying hybridizing fragments differing in length from control DNA when probed with sequences near or including the CtIP locus indicate a possible mutation. If restriction enzymes which produce very large restriction fragments are used, then pulsed field gel electrophoresis (PFGE) is employed.

Detection of point mutations may be accomplished by molecular cloning of the CtIP allele and sequencing the allele using techniques well known in the art.

There are six well known methods for a more complete, yet still indirect, test for confirming the presence of a susceptibility allele: 1) single stranded conformation analysis (SSCP) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the E. coli mutS protein (Modrich, 1991); and 6) allele-specific PCR (Rano and Kidd, 1989). For allele-specific PCR, primers are used which hybridize at their 3' ends to a particular CtIP mutation. If the particular mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type CtIP gene coding sequence. The riboprobe and either mRNA or DNA isolated from the person are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene but can be a segment of either. If the riboprobe comprises only a segment of the mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton et al., 1988; Shenk et al., 1975; Novack et al., 1986. Alternatively, mismatches can be detected by shifts in the electrophoretic mobility of mismatched duplexes relative to matched duplexes. See, e.g., Cariello, 1988. With either riboprobes or DNA probes, the cellular mRNA or DNA which might contain a mutation can be amplified using PCR (see below) before hybridization. Changes in DNA of the CtIP gene can also be detected using Southern hybridization, especially if the changes are gross rearrangements, such as deletions and insertions.

DNA sequences of the CtIP gene which have been amplified by use of PCR may also be screened using allele-specific probes. These probes are nucleic acid oligomers, each of which contains a region of the gene sequence harboring a known mutation. For example, one oligomer may be about 30 nucleotides in length, corresponding to a portion of the gene sequence. By use of a battery of such allele-specific probes, PCR amplification products can be screened to identify the presence of a previously identified mutation in the gene. Hybridization of allele-specific probes with amplified CtIP sequences can be performed, for example, on a nylon filter. Hybridization to a particular probe under high stringency hybridization conditions indicates the presence of the same mutation in the tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescently labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Nature Genetics, 1996). Also see Fodor (1997).

The most definitive test for mutations in a candidate locus is to directly compare genomic CtIP sequences from patients with those from a control population. Alternatively, one could sequence messenger RNA after amplification, e.g., by PCR, thereby eliminating the necessity of determining the exon structure of the candidate gene.

Mutations from patients falling outside the coding region of CtIP can be detected by examining the non-coding regions, such as introns and regulatory sequences near or within the genes. An early indication that mutations in noncoding regions are important may come from Northern blot experiments that reveal messenger RNA molecules of abnormal size or abundance in patients as compared to control individuals.

Alteration of CtIP mRNA expression can be detected by any techniques known in the art. These include Northern blot analysis, PCR amplification and RNase protection. Diminished mRNA expression indicates an alteration of the wild-type gene. Alteration of wild-type genes can also be detected by screening for alteration of wild-type CtIP protein. For example, monoclonal antibodies immunoreactive with CtIP can be used to screen a tissue. Lack of cognate antigen would indicate a mutation. Antibodies specific for products of mutant alleles could also be used to detect mutant gene product. Such immunological assays can be done in any convenient formats known in the art. These include Western blots, immunohistochemical assays and ELISA assays. Any means for detecting an altered CtIP protein can be used to detect alteration of the wild-type CtIP gene. Functional assays, such as protein binding determinations, can be used. In addition, assays can be used which detect CtIP biochemical function. Finding a mutant CtIP gene product indicates alteration of a wild-type CtIP gene.

A mutant CtIP gene or gene product can also be detected in other human body samples, such as serum, stool, urine and sputum. The same techniques discussed above for detection of mutant genes or gene products in tissues can be applied to other body samples. By screening such body samples, a simple early diagnosis can be achieved for cancer resulting from a mutation in the CtIP gene.

The primer pairs of the present invention are useful for determination of the nucleotide sequence of a particular CtIP allele using PCR. The pairs of single-stranded DNA primers for CtIP can be annealed to sequences within or surrounding the CtIP gene in order to prime amplifying DNA synthesis of the gene itself A complete set of these primers allows synthesis of all of the nucleotides of the gene coding sequences, i.e., the exons. The set of primers preferably allows synthesis of both intron and exon sequences. Allele-specific primers can also be used. Such primers anneal only to particular CtIP mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from CtIP sequence or sequences adjacent to CtIP, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of CtIP, design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the CtIP gene or mRNA using other techniques.

Mutations which interfere with the function of the CtIP gene product are involved in the pathogenesis of cancer. Thus, the presence of an altered (or a mutant) CtIP gene which produces a protein having a loss of function, or altered function, directly increases the risk of cancer. In order to detect a CtIP gene mutation, a biological sample is prepared and analyzed for a difference between the sequence of the allele being analyzed and the sequence of the wild-type allele. Mutant CtIP alleles can be initially identified by any of the techniques described above. The mutant alleles are then sequenced to identify the specific mutation of the particular mutant allele. Alternatively, mutant alleles can be initially identified by identifying mutant (altered) proteins, using conventional techniques. The mutant alleles are then sequenced to identify the specific mutation for each allele. The mutations, especially those which lead to an altered function of the protein, are then used for the diagnostic and prognostic methods of the present invention.

Screening of several tumor cell lines has revealed the presence of several mutations. Mutations which interfere with the function of the CtIP gene product are involved in the pathogenesis of cancer. Thus, the presence of an altered (or a mutant) CtIP gene which produces a protein having a loss of function, or altered function, directly increases the risk of cancer. In order to detect a CtIP gene mutation, a biological sample is prepared and analyzed for a difference between the sequence of the allele being analyzed and the sequence of the wild-type allele. Mutant CtIP alleles can be initially identified by any of the techniques described above. The mutant alleles are then sequenced to identify the specific mutation of the particular mutant allele. Alternatively, mutant alleles can be initially identified by identifying mutant (altered) proteins, using conventional techniques. The mutant alleles are then sequenced to identify the specific mutation for each allele. The mutations, especially those which lead to an altered function of the protein, are then used for the diagnostic and prognostic methods of the present invention.

Definitions

The present invention employs the following definitions.

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al., 1990 (for PCR); Wu et al., 1989a (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the CtIP region are preferably complementary to, and hybridize specifically to sequences in the CtIP region or in regions that flank a target region therein. CtIP sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf, 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the CtIP polypeptide and fragments thereof or to polynucleotide sequences from the CtIP region. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the CtIP polypeptide or fragment. Monoclonal antibodies may be made by injecting mice with the protein polypeptides, fusion proteins or fragments thereof. Monoclonal antibodies will be screened by ELISA and tested for specific immunoreactivity with CtIP polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermnally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^9$ to $10^{-10}$ $M^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"CtIP Allele" refers to normal alleles of the CtIP locus as well as alleles of CtIP carrying variations that cause cancer.

"CtIP Locus", "CtIP Gene", "CtIP Nucleic Acids" or "CtIP Polynucleotide" each refer to polynucleotides, all of which are in the CtIP region, that are likely to be expressed in normal tissue, certain alleles of which result in cancer. The CtIP locus is intended to include coding sequences, intervening sequences and regulatory elements controlling transcription and/or translation. The CtIP locus is intended to include all allelic variations of the DNA sequence.

These terms, when applied to a nucleic acid, refer to a nucleic acid which encodes a human CtIP polypeptide, fragment, homolog or variant, including, e.g., protein fusions or deletions. The nucleic acids of the present invention will possess a sequence which is either derived from, or substantially similar to a natural CtIP-encoding gene or one having substantial homology with a natural CtIP-encoding gene or a portion thereof.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the CtIP region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature.

Therefore, recombinant nucleic acids comprising sequences otherwise not naturally occurring are provided by this invention. Although the wild-type sequence may be employed, it will often be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with a CtIP-encoding sequence.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promega, U. S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, a "portion" of the CtIP locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides.

"CtIP protein" or "CtIP polypeptide" refers to a protein or polypeptide encoded by the CtIP locus, variants or fragments thereof The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native CtIP sequence, preferably in excess of about 90%, and more preferably at least about 95% homologous. Also included are proteins encoded by DNA which hybridize under high or low stringency conditions, to CtIP-encoding nucleic acids and closely related polypeptides or proteins retrieved by antisera to the CtIP protein(s).

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

"Probes". Polynucleotide polymorphisms associated with CtIP alleles which predispose to cancer are detected by hybridization with a polynucleotide probe which forms a stable hybrid with that of the target sequence, under highly stringent to moderately stringent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that is meant to be read as "high stringency" conditions are used.) Since such indications identify neutral DNA polymorphisms as well as mutations, these indications need further analysis to demonstrate detection of a CtIP susceptibility allele.

Probes for CtIP alleles may be derived from the sequences of the CtIP region or its cDNA. The probes may be of any suitable length, which span all or a portion of the CtIP region, and which allow specific hybridization to the region. If the target sequence contains a sequence identical to that of the probe, the probes may be short, e.g., in the range of about 8–30 base pairs, since the hybrid will be relatively stable under even highly stringent conditions. If some degree of mismatch is expected with the probe, i.e., if it is suspected that the probe will hybridize to a variant region, a longer probe may be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent changes (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes may also be labeled by nick translation, Klenow fill-in reaction, or other methods known in the art.

Portions of the polynucleotide sequence having at least about eight nucleotides, usually at least about 15 nucleotides, and fewer than about 6 kb, usually fewer than about 1.0 kb, from a polynucleotide sequence encoding CtIP are preferred as probes. This definition therefore includes probes of sizes 8 nucleotides through 6000 nucleotides. The probes may also be used to determine whether mRNA encoding CtIP is present in a cell or tissue.

"Protein modifications or fragments" are provided by the present invention for CtIP polypeptides or fragments thereof which are substantially homologous to primary structural sequence but which include, e.g., in vivo or in vitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are well known in the art, and include radioactive isotopes such as $^{32}P$, ligands which bind to labeled antiligands (e.g., antibodies), fluorophores, chemiluminescent agents, enzymes, and antiligands which can serve as specific binding pair members for a labeled ligand. The choice of label depends on the sensitivity required, ease of conjugation with the primer, stability requirements, and available instrumentation. Methods of labeling polypeptides are well known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of CtIP polypeptides. Immunological activities include both immunogenic function in a target immune system, as well as sharing of immunological epitopes for binding, serving as either a competitor or substitute antigen for an epitope of the CtIP protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for CtIP polypeptides or fragments thereof is described below.

The present invention also provides for fusion polypeptides, comprising CtIP polypeptides and fragments. Homologous polypeptides may be fusions between two or more CtIP polypeptide sequences or between the sequences of CtIP and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See Godowski et al., 1988.

Fusion proteins will typically be made by either recombinant nucleic acid methods, as described below, or may be chemically synthesized. Techniques for the synthesis of polypeptides are described, for example, in Merrifield, 1963.

"Protein purification" refers to various methods for the isolation of the CtIP polypeptides from other biological material, such as from cells transformed with recombinant nucleic acids encoding CtIP, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

A CtIP protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide," as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulatory sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameter. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, and preferably at least about 95% identity.

"Substantially similar function" refers to the function of a modified nucleic acid or a modified protein, with reference to the wild-type CtIP nucleic acid or wild-type CtIP polypeptide. The modified polypeptide will be substantially homologous to the wild-type CtIP polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type CtIP polypeptide. Alternatively, the similarity of function (activity) of the modified polypeptide may be higher than the activity of the wild-type CtIP polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type CtIP gene function produces the modified protein described above.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measure of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

A polypeptide "fragment," "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985; Anand, 1992; Guthrie and Fink, 1991. A general discussion of techniques and materials for human gene mapping, including mapping of human chromosome 1, is provided, e.g., in White and Lalouel, 1988.

Preparation of Recombinant or Chemically Synthesized Nucleic Acids; Vectors, Transformation, Host Cells Large amounts of the polynucleotides of the present invention may be produced by replication in a suitable host cell. Natural or synthetic polynucleotide fragments coding for a desired fragment will be incorporated into recombinant polynucleotide constructs, usually DNA constructs, capable of introduction into and replication in a prokaryotic or eukaryotic cell. Usually the polynucleotide constructs will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention are described, e.g., in Sambrook et al., 1989 or Ausubel et al., 1992.

The polynucleotides of the present invention may also be produced by chemical synthesis, e.g., by the phosphoramidite method described by Beaucage and Carruthers, 1981 or the triester method according to Matteucci and Caruthers, 1981, and may be performed on commercial, automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or eukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, B transcriptional terminator sequences, and mRNA stabilizing sequences. Such vectors may be prepared by means of standard recombinant techniques well known in the art and discussed, for example, in Sambrook et al., 1989 or Ausubel et al., 1992.

An appropriate promoter and other necessary vector sequences will be selected so as to be functional in the host, and may include, when appropriate, those naturally associated with the CtIP gene. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Molony leukemia virus, mouse tumor virus, avian sarcoma viruses, adenovirus II, bovine papilloma virus or polyoma. In addition, the construct may be joined to an amplifiable gene (e.g., DHFR) so that multiple copies of the gene may be made. For appropriate enhancer and other expression control sequences, see also Enhancers and Eukaryotic Gene Expression, Cold Spring Harbor Press, Cold Spring Harbor, New York (1983).

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed in vitro, and the resulting RNA introduced into the host cell by well-known methods, e.g., by injection (see, Kubo et al., 1988), or the vectors can be introduced directly into host cells by methods well known in the art, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the CtIP nucleic acid or portions thereof in vectors or other expression vehicles in compatible prokaryotic or eukaryotic host cells. The most commonly used prokaryotic hosts are strains of *Escherichia coli,* although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.), 1979. Examples of commonly used mammalian host cell lines are VERO and HeLa cells, Chinese hamster ovary (CHO) cells, and W138, BHK, and COS cell lines, although it will be appreciated by the skilled practitioner that other cell lines may be appropriate, e.g., to provide higher expression, desirable glycosylation patterns, or other features.

Clones are selected by using markers depending on the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of CtIP polypeptide.

The probes and primers based on the CtIP gene sequence disclosed herein are used to identify homologous CtIP gene sequences and proteins in other species. These gene sequences and proteins are used in the diagnostic/prognostic, therapeutic and drug screening methods described herein for the species from which they have been isolated.

Methods of Use: Drug Screening

This invention is particularly useful for screening compounds by using the CtIP polypeptide or binding fragment thereof in any of a variety of drug screening techniques.

The CtIP polypeptide or fragment employed in such a test may either be free in solution, affixed to a solid support, or borne on a cell surface. One method of drug screening utilizes eukaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a CtIP polypeptide or fragment and the agent being tested, or examine the degree to which the formation of a complex between a CtIP polypeptide or fragment and a known ligand, e.g., BRCA1, is aided or interfered with by the agent being tested.

Thus, the present invention provides methods of screening for drugs comprising contacting such an agent with a CtIP polypeptide or fragment thereof and assaying (i) for the presence of a complex between the agent and the CtIP polypeptide or fragment, or (ii) for the presence of a complex between the CtIP polypeptide or fragment and a ligand, by methods well known in the art. In such competitive binding assays the CtIP polypeptide or fragment is typically labeled. Free CtIP polypeptide or fragment is separated from that present in a protein:protein complex, and the amount of free (i.e., uncomplexed) label is a measure of the binding of the agent being tested to CtIP or its interference with or promotion of CtIP:ligand binding, respectively. One may also measure the amount of bound, rather than free, CtIP. It is also possible to label the ligand rather than the CtIP and to measure the amount of ligand binding to CtIP in the presence and in the absence of the drug being tested.

Another technique for drug screening provides high throughput screening for compounds having suitable binding affinity to the CtIP polypeptides and is described in detail in Geysen, PCT published application WO 84/03564, published on Sep. 13, 1984. Briefly stated, large numbers of different small peptide test compounds are synthesized on a solid substrate, such as plastic pins or some other surface. The peptide test compounds are reacted with CtIP polypeptide and washed. Bound CtIP polypeptide is then detected by methods well known in the art.

Purified CtIP can be coated directly onto plates for use in the aforementioned drug screening techniques. However, non-neutralizing antibodies to the polypeptide can be used to capture antibodies to immobilize the CtIP polypeptide on the solid phase.

This invention also contemplates the use of competitive drug screening assays in which neutralizing antibodies capable of specifically binding the CtIP polypeptide compete with a test compound for binding to the CtIP polypeptide or fragments thereof. In this manner, the antibodies can be used to detect the presence of any peptide which shares one or more antigenic determinants of the CtIP polypeptide.

The above screening methods are not limited to assays employing only CtIP but are also applicable to studying CtIP-protein complexes, e.g., the complex which occurs between CtIP and BRCA1. The effect of drugs on the activity of this complex, especially when either the CtIP or the CtIP binding protein (e.g., BRCA1) contains a mutation, is analyzed.

Methods of Use: Nucleic Acid Diagnosis and Diagnostic Kits

In order to detect the presence of a CtIP allele predisposing an individual to cancer, a biological sample such as blood is prepared and analyzed for the presence or absence of susceptibility alleles of CtIP. In order to detect the presence of cancer or as a prognostic indicator, a biological sample is prepared and analyzed for the presence or absence of mutant alleles of CtIP. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant CtIP sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences the biological sample to be analyzed, such as blood or serum, may be treated, if desired, to extract the nucleic acids. The sample nucleic acid may be prepared in various ways to facilitate detection of the target sequence, e.g., denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region for CtIP. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; U.S. Pat. No. 4,868,105; and in EPO Publication No. 225, 807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes, see Jablonski et al., 1986.

Two-step label amplification methodologies are known in the art. These assays work on the principle that a small ligand (such as digoxigenin, biotin, or the like) is attached to a nucleic acid probe capable of specifically binding CtIP. Allele specific probes are also contemplated within the scope of this example and exemplary allele specific probes include probes encompassing the predisposing mutations of this disclosure.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting CtIP. Thus, in one example to detect the presence of CtIP in a cell sample, more than one probe complementary to the gene is employed and in particular the number of different probes is alternatively two, three, or five different nucleic acid probe sequences. In another example, to detect the presence of mutations in the CtIP gene sequence in a patient, more than one probe complementary to these genes is employed where the cocktail includes probes capable of binding to the allele-specific mutations identified in populations of patients with alterations in CtIP. In this embodiment, any number of probes can be used, and will preferably include probes corresponding to the major gene mutations identified as predisposing an individual to cancer.

Methods of Use: Peptide Diagnosis and Diagnostic Kits

The presence of cancer can also be detected on the basis of the alteration of wild-type CtIP polypeptide. Such alterations can be determined by sequence analysis in accordance with conventional techniques. More preferably, antibodies (polyclonal or monoclonal) are used to detect differences in, or the absence of CtIP peptides. Techniques for raising and purifing antibodies are well known in the art and any such techniques may be chosen to achieve the preparations claimed in this invention. In a preferred embodiment of the invention, antibodies will immunoprecipitate CtIP proteins from solution as well as react with these proteins on Western or immunoblots of polyacrylamide gels. In another preferred embodiment, antibodies will detect CtIP proteins in paraffin or frozen tissue sections, using immunocytochemical techniques.

Preferred embodiments relating to methods for detecting CtIP or its mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486,530, hereby incorporated by reference.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., CtIP polypeptide) by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., CtIP polypeptide) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved CtIP polypeptide activity or stability or which act as inhibitors, agonists, antagonists, etc. of CtIP polypeptide activity. By virtue of the availability of cloned CtIP sequence, sufficient amounts of the CtIP polypeptide may be made available to perform such analytical studies as x-ray crystallography. In addition, the knowledge of the CtIP protein sequence provided herein will guide those employing computer modeling techniques in place of, or in addition to x-ray crystallography.

Methods of Use: Gene Therapy

According to the present invention, a method is also provided of supplying wild-type CtIP function to a cell which carries a mutant CtIP allele. Supplying such a function should allow normal functioning of the recipient cells. The wild-type gene or a part of the gene may be introduced into the cell in a vector such that the gene remains extrachromosomal. In such a situation, the gene will be expressed by the cell from the extrachromosomal location. More preferred is the situation where the wild-type gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner.

As generally discussed above, the CtIP gene or fragment, where applicable, may be employed in gene therapy methods in order to increase the amount of the expression products of such gene in cells. It may also be useful to increase the level of expression of the CtIP gene even in those persons in which the mutant gene is expressed at a "normal" level, but the gene product is not fully functional.

Gene therapy would be carried out according to generally accepted methods, for example, as described by Friedman, 1991. Cells from a patient would be first analyzed by the diagnostic methods described above, to ascertain the production of CtIP polypeptide in the cells. A virus or plasmid vector (see further details below), containing a copy of the CtIP gene linked to expression control elements and capable of replicating inside the cells, is prepared. Suitable vectors are known, such as disclosed in U.S. Pat. No. 5,252,479 and PCT published application WO 93/07282. The vector is then injected into the patient. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson et al., 1992; Stratford-Perricaudet et al., 1990), vaccinia virus (Moss, 1992), adeno-associated virus (Muzyczka, 1992; Ohi et al., 1990), herpesviruses including HSV and EBV (Margolskee, 1992; Johnson et al., 1992; Fink et al., 1992; Breakfield and Geller, 1987; Freese et al., 1990), and retroviruses of avian (Brandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Constantini and Lacy, 1981); membrane fusion-mediated transfer via liposomes (Feigner et al., 1987; Wang and Huang, 1989; Kaneda et al., 1989; Stewart et al., 1992; Nabel et al., 1990; Lim et al., 1992); and direct DNA uptake and receptor-mediated DNA transfer (Wolff et al., 1990; Wu et al., 1991; Zenke et al., 1990; Wu et al., 1989b; Wolff et al., 1991; Wagner et al., 1990; Wagner et al., 1991; Cotten et al., 1990; Curiel et al., 1991a; Curiel et al., 1991b).

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Gene transfer techniques which target DNA directly to brain tissue is preferred. Receptor—mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy is as follows: patients who carry a CtIP susceptibility allele are treated with a gene delivery vehicle such that some or all of their brain precursor cells receive at least one additional copy of a functional normal CtIP allele, respectively. In this step, the treated individuals have reduced risk of cancer to the extent that the effect of the susceptible allele has been countered by the presence of the normal allele.

Methods of Use: Peptide Therapy

Peptides which have CtIP activity can be supplied to cells which carry a mutant or missing CtIP allele. Protein can be produced by expression of the cDNA sequence in bacteria, for example, using known expression vectors. Alternatively, CtIP polypeptide can be extracted from CtIP-producing mammalian cells. In addition, the techniques of synthetic chemistry can be employed to synthesize CtIP protein. Any of such techniques can provide the preparation of the present invention which comprises the CtIP protein. The preparation is substantially free of other human proteins. This is most readily accomplished by synthesis in a microorganism or in vitro.

Active CtIP molecules can be introduced into cells by microinjection or by use of liposomes, for example. Alternatively, some active molecules may be taken up by cells, actively or by diffusion. Supply of molecules with CtIP activity should lead to inhibition of cancer. Other molecules with CtIP activity (for example, peptides, drugs or organic compounds) may also be used to effect such an inhibition. Modified polypeptides having substantially similar function are also used for peptide therapy.

Methods of Use: Transformed Hosts

Animals for testing therapeutic agents can be selected after mutagenesis of whole animals or after treatment of germline cells or zygotes. Such treatments include insertion of mutant CtIP alleles, usually from a second animal species, as well as insertion of disrupted homologous genes. Alternatively, the endogenous CtIP gene of the animals may be disrupted by insertion or deletion mutation or other genetic alterations using conventional techniques (Capecchi, 1989; Valancius and Smithies, 1991; Hasty et al., 1991; Shinkai et al., 1992; Mombaerts et al., 1992; Philpott et al., 1992; Snouwaert et al., 1992; Donehower et al., 1992). After test substances have been administered to the animals, the presence of cancer must be assessed. If the test substance prevents or suppresses the appearance of cancer, then the test substance is a candidate therapeutic agent for treatment of cancer. These animal models provide an extremely important testing vehicle for potential therapeutic products.

The identification of the association between the CtIP gene mutations and cancer permits the early presymptomatic screening of individuals to identify those at risk for developing cancer. To identify such individuals, CtIP alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO), dot blot analysis and PCR-SSCP analysis. Also useful is the recently developed technique of DNA microchip technology. For example, either (1) the nucleotide sequence of both the cloned alleles and normal CtIP gene or appropriate fragment (coding sequence or genomic sequence) are determined and then compared, or (2) the RNA transcripts of the CtIP gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the CtIP gene in an individual to be tested are cloned using conventional techniques. For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal CtIP gene.

Alternatively, polymerase chain reactions (PCRs) are performed with primer pairs for the 5' region or the exons of the CtIP gene. PCRs can also be performed with primer pairs based on any sequence of the normal CtIP gene. For example, primer pairs for one of the introns can be prepared and utilized. Finally, PCR can also be performed on the mRNA. The amplified products are then analyzed by single stranded conformation polymorphisms (SSCP) using conventional techniques to identify any differences and these are then sequenced and compared to the normal gene sequence.

Individuals can be quickly screened for common CtIP gene variants by amplifying the individual's DNA using suitable primer pairs and analyzing the amplified product, e.g., by dot-blot hybridization using allele-specific oligonucleotide probes.

The second method employs RNase A to assist in the detection of differences between the normal CtIP gene and defective genes. This comparison is performed in steps using small (~500 bp) restriction fragments of the CtIP gene as the probe. First, the CtIP gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing inserts of the CtIP gene fragments are transcribed in vitro using the SP6 transcription system, well known in the art, in the presence of [α-$^{32}$P]GTP, generating radiolabeled RNA transcripts of both strands of the gene.

Individually, these RNA transcripts are used to form heteroduplexes with the allelic DNA using conventional techniques. Mismatches that occur in the RNA:DNA heteroduplex, owing to sequence differences between the CtIP fragment and the CtIP allele subclone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Any differences which are found, will identify an individual as having a molecular variant of the CtIP gene and the consequent presence of cancer. These variants can take a number of forms. The most severe forms would be frame shift mutations or large deletions which would cause the gene to code for an abnormal protein or one which would significantly alter protein expression. Less severe disruptive mutations would include small in-frame deletions and non-conservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Genetic testing will enable practitioners to identify individuals at risk for cancer at, or even before, birth. Finally, this invention changes our understanding of the cause and treatment of cancer.

The present invention is further detailed in the following Examples, which are offered by way of illustration and are not intended to limit the invention in any manner. Standard techniques well known in the art or the techniques specifically described below are utilized.

EXAMPLE 1

Yeast Two-Hybrid Assay

A BRCA1 carboxy-terminal segment from amino acid residue 1602 to 1863 was cloned into the Gal4p DNA-binding domain vector pGBT.C (Bartel et al., 1996). This construct was used to screen an EBV-transformed B-cell cDNA library prepared in an activation domain vector (Clontech Laboratories, Catalog Number HL4006AE). After co-transformation into the yeast strain J692, cells were plated on yeast minimal medium lacking tryptophan, leucine, and histidine and including 25 mM 3-amino-1,2,4-triazole (Gietz et al., 1995; Bartel and Fields, 1995). After the plates were incubated for approximately 8 days at 30° C., β-galactosidase activity was determined by a filter assay (Breeden and Naysmyth, 1985). Positive colonies were blue in appearance. The relative strengths of β-galactosidase activities were scored as +++ (strong), + (weak), or – (none).

140 His$^+$ colonies were identified from the B-cell library search. The clone B112 was digested with XhoI releasing the 1.2 kb DNA fragment that encodes amino acid residues 312–712 of CtIP. This fragment was subcloned into the Gal4p DNA-binding domain fusion vector, pGBT.C and Gal4p activation domain vector, pGAD.C. Similar constructs were made with BRCA1 fragments from amino acid residues 1602–1863 and 1602–1852. They were co-transformed in all pairwise combinations. All clones were confirmed by sequencing using the dideoxy termination method (Sanger et al, 1977).

In the yeast two-hybrid searches, the carboxy-terminus of BRCA1 from amino acid residue 1602 to amino acid residue 1863 was expressed as a Gal4p DNA-binding domain fusion. This construct was used to search an EBV-transformed human B-cell cDNA library that was prepared in a Gal4p activation domain vector. One of the isolated His$^+$ colonies, designated as B112, that was positive in the β-galactosidase assay was chosen for further characterization. Because the BRCA1 protein in the Gal4p DNA-binding fusion could self-activate weakly resulting in background activity of the reporter β-galactosidase, a number of controls were performed to verify that interaction with the B112 protein is specific. The insert from clone B112 and the carboxy terminal segment of BRCA1 were swapped into Gal4p DNA-binding and activation domain vector for analysis in all pairwise combinations by co-transformation in yeast. As shown in Table 1, the interaction of BRCA1 DNA-binding domain fusion with B112 activation domain fusion resulted in stronger β-galactosidase activity than the activity that was generated by the BRCA1 DNA-binding domain fusion alone. Placement of BRCA1 in the activation domain vector pGAD.C eliminated the problem of self-activation. Strong β-galactosidase activity was also observed when this construct was co-transformed with B112 in the DNA-binding domain plasmid pGBT.C. As an additional control, B112 activation domain fusion was tested against a non-specific target, lamin C. The yeast transformants harboring these two fusions were negative in the β-galactosidase assay (Table 1).

Familial mutations are found in the carboxy-terminal segment of BRCA1. One of these mutations, 1853ter, has an insertion of an A introducing a stop codon which effectively removes the last 11 amino acids of the wild-type protein. To determine whether the 1853ter mutation could perturb the interaction of BRCA1 with CtIP, the BRCA1 fragment missing the last 11 amino acids

TABLE 1

| Binding Domain Plasmid (pGBT.C) | Activation Domain Plasmid (pGAD.C) | β-Galactosidase Assay |
| --- | --- | --- |
| No Insert | No Insert | − |
| No Insert | wt-BRCA1 | − |
| No Insert | B112 (CtIP) | − |
| wt-BRCA1 | No Insert | + |
| B112 (CtIP) | No Insert | − |
| wt-BRCA1 | B112 (CtIP) | +++ |
| B112 (CtIP) | wt-BRCA1 | +++ |
| Lamin C | B112 (CtIP) | − |
| 1853ter-BRCA1 | No Insert | − |
| No Insert | 1853ter-BRCA1 | − |
| 1853ter-BRCA1 | B112 (CtIP) | − |
| B112 (CtIP) | 1853ter-BRCA1 | − | wt-BRCA1 refers to the 1602–1863 fragment of BRCA1
1853ter-BRCA1 refers to the 1602–1852 fragment of BRCA1
B112 (CtIP) refers to the 312–712 fragment of B112 (CtIP)

was generated by PCR and cloned into the Gal4p DNA binding domain and activation domain vector. The wild type and mutant BRCA1 constructs were cotransformed with CtIP-Gal4p fusions in yeast. As shown in Table 1, the mutant BRCA1 1853ter (the 1602–1852 fragment was used in the assay for this), did not interact with CtIP (the 312–712 fragment was used in the assay for this) in either Gal4p-DNA binding or activation domain fusion context. It was found that the removal of the 11 amino acid residues abolished the weak self-activation phenotype when BRCA1 is placed in the Gal4p DNA binding domain vector. In these transformants, β-galactosidase activity was not observed.

EXAMPLE 2

In Vitro Protein—protein Interaction Assay

Wild type BRCA1 (amino acid residues 1602 to 1863), 1853ter mutant BRCA1 (amino acid residues 1602–1852), CtIP segment A (amino acid residues 324–584) and CtIP segment B (amino acid residues 324–697) were generated by PCR and subcloned as glutathione S-transferase (GST) fusions in pGEX vectors (Pharmacia). These constructs were designated as GST-wt-BRCA1, GST-mu-BRCA1, GST-CtIPa, and GST-CtIPb, respectively. GST-fusion proteins were synthesized in E. coli strain BL21(DE3)pLysS (Stratagene) and purified by adsorption to glutathione-Sepharose beads. For the production of radiolabeled full length BRCA1 and β-galactosidase, they were first cloned in the pCITE translation expression vector (Novagen). In the case of B112, the insert containing amino acid residues 312–712, identified as a region that interacts with BRCA1 in the yeast two-hybrid assay, was amplified by PCR with the forward primer containing the T7 promoter sequence. In vitro syntheses of B112, BRCA1 and β-galactosidase RNAs were carried out with T7 RNA polymerase (Sambrook et al., 1989). They were then in vitro translated in the presence of 35S methionine using a rabbit reticulocyte lysate kit from Promega. Equal amounts of GST and GST fusion proteins, as determined by Coomassie Blue staining of aliquots run on gels, were used in each binding assay. The radiolabeled proteins were incubated with GST and GST-fusions bound on beads for an hour at 4° C. with gentle rocking according to the protocol of Sande and Privalsky, 1996. The protein complexes were extensively washed to eliminate non-specific protein interactions and released by heating to 90° C. in an equal volume of 2×SDS-PAGE loading buffer. The radiolabeled proteins were analyzed by SDS-PAGE and visualized by autoradiography.

Figure 2A:
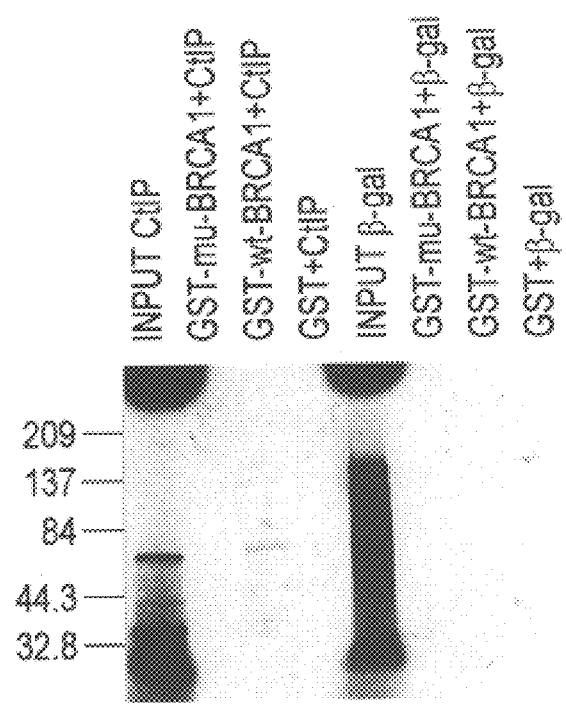
FIGS. 2A–B. In vitro binding of BRCA1 to B112 (CtIP). Similar amounts of GST and GST-fusion proteins immobilized on glutathione-Sepharose beads (100 μl) were incubated with 15 μl of in vitro translated $^{35}$S radiolabeled proteins. (A) Wild type and mutant BRCA1 expressed as GST fusions (GST-wt-BRCA1 and GST-mu-BRCA1) were incubated with radiolabeled B112 protein (residues 312–712) and with β-galactosidase. (B) Two different segments of protein B112 expressed as GST fusions (GST-B112a and GST-B112b) were incubated with radiolabeled BRCA1 and with β-galactosidase. In both A and B, non-recombinant GST was reacted with all radiolabeled proteins. After washing four times with buffer, the beads were resuspended in 30 μl of 2×SDS-PAGE loading dye, boiled and spun. 20 μl of the supernatant was resolved by SDS-PAGE. The input radiolabeled protein in each panel represents the control sample before incubation with GST or GST-fusions. Molecular weight markers are as indicated.
Figure 2B:
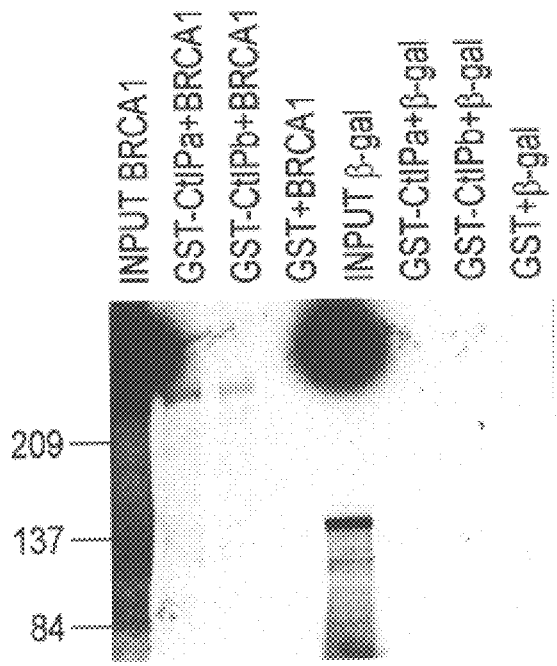

The GST-affinity pull down assay is a complementary in vitro method for investigating protein—protein interactions. To ascertain that the interaction between BRCA1 and the CtIP protein was direct and to show that the 1853ter mutant's inability to interact in the yeast two hybrid assay was not due to lack of protein expression, the wild type BRCA1 (amino acid residues 1602 to 1863) and mutant BRCA1, 1853ter (amino acid residues 1602–1852) were prepared as GST fusions for testing in vitro. Amino acid residues 312–712 of protein CtIP, identified as a region that interacts with BRCA1 in the yeast two-hybrid assay, were radiolabeled by in vitro trasation and used as the target for the binding assays. Radiolabeled CtIP protein was incubated with non-recombinant OST, wild type GST-BRCA1 and mutant GST-mu-BRCA1, all of which were immobilized by adsorption to glutathione-Sepharose beads. After extensive washings, only the proteins that bound specifically should be detected. As shown in FIG. 2A, the radiolabeled CtIP protein was found to interact with the wild type fusion GST-wt-BRCA1, but not to mutant GST-mu-BRCA1 or non-recombinant GST. Additional binding experiments were also performed in which the CtIP protein prepared as GST fusions were reacted with radiolabeled BRCA1. Two segments of the protein CtIP, amino acid residues 324–584 (GST-CtIPa) and 324–697 (GST-CtIPb) were expressed as GST fusions. It was found that the wild-type BRCA1 could bind specifically to both GST-CtIP fusions in the in vitro binding assays (FIG. 2B). The region of CtIP interaction with BRCA1 was delimited to between amino acid residues 324 and 584. As negative controls, the enzyme β-galactosidase, which should not interact with BRCA1 or CtIP protein, was radiolabeled and analyzed under the same set of in vitro binding conditions. The radiolabeled β-galactosidase was not significantly retained by non-recombinant OST or any of the GST fusion proteins (FIGS. 2A and B).

EXAMPLE 3

Northern Blot and RACE

A multi-tissue RNA blot (Clontech Laboratories) was hybridized with $^{32}$P-labeled probes of B I 12 and glyceraldehyde 3-phosphate dehydrogenase (G3PDH) using standard techniques (Sambrook et al., 1989). To obtain the missing ends of B112 cDNA, RACE was performed using the Marathon-Ready premade testis cDNA pools (Clontech Laboratories). Testis was chosen as a source for PCR, because B112 expression was highest in that tissue. The gene specific primer for 5' RACE was 5'-ATGATCTTGTTCACTTCAGACCCAAGAC-3' (SEQ ID NO: 1) and for 3' RACE was 5'-TCCTCTACGTCCACGTGAAAGTTTG-3' (SEQ ID NO:2). Full length CtIP cDNA was obtained by gene amplification using normal and tumor breast cDNA pools as templates and the following primer pair: forward-5'-

GCGAAAGAGAAAAGCGAGCAGCCG-3' (SEQ ID NO:3) and reverse-5'-GAGTGCAAAATGAAAGCGCCTTATTG-3' (SEQ ID NO:4). The RACE products and full length cDNA were gel purified and sequenced directly.

Figure 1B:
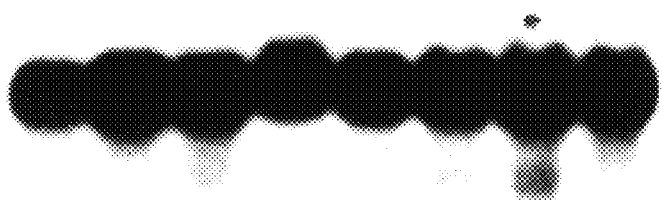

Next the size, distribution, and abundance of the BRCA1 interacting protein gene B112 were determined at the RNA level. Northern analysis revealed that the mRNA is approximately 3.2 kb in size (FIG. 1A). It was expressed in a variety of tissues—spleen, thymus, prostate, testis, ovary, small intestine, colon and blood leukocyte. Of the eight tissues tested, the highest level of expression was found in testis followed by thymus. This difference was not due to sample loading variations as is shown by the fact that the internal control G3PDH is relatively equal in all samples (FIG. 1B). B112 mRNA was also expressed in breast tissue (data not shown). Because the clone B112 was contained only a 1.2 kb insert, RACE was performed to obtain the missing 5' and 3' ends. Gene amplification with normal and tumor breast cDNA pools was used to generate full length templates for complete DNA sequence analysis. An open reading frame of 2694 bp was identified. While this work was in progress, a gene sequence referred to as CtIP was deposited in GenBank (Accession No. U72066) which is identical to the B112 sequence except at nucleotide position 11. The fourth codon of the B112 sequence is TCG, which encodes serine, whereas the GenBank Accession No. U72066 sequence reports the fourth codon as TTG, which encodes leucine. The cDNA sequence for B112 is shown as SEQ ID NO:5 and the amino acid sequence for the B112 encoded protein is shown as SEQ ID NO:6. It is not clear if this change is due to a rare sequence polymorphism or an error in the previous report. The sequence of SEQ ID NO:5 is based on the consensus obtained from sequencing the gene from multiple cDNA sources. The base difference occurs within an Asn-glycosylation motif, NISG (SEQ ID NO:41). It is presumed that replacement of serine with a leucine residue could eliminate N-glycosylation at that site. Furthermore, two bases in the 5' untranslated region and one base in the 3' untranslated region were found in the present studies that are not found in the sequence of GenBank Accession No. U72066. For uniformity, the name CtIP is adopted for the BRCA1 interacting protein B112.

Of interest is the recognition that the CtIP protein has several putative nuclear localization signals (Hicks et al., 1995; Gorlick, 1997). These are of two types: pattern 4 and pattern 7. These putative signals are as follows with the location of the first amino acid residue being noted: KKKH at 355, KRKK at 446, RPKR at 877 and PKRR at 878 (all of pattern 4) and PGKKKHL at 353, PCPRPKR at 874, PRPKRRQ at 876 and PKRRQPY at 878 (all of pattern 7).

EXAMPLE 4

Mutation Screening of B112 cDNA

Human tumor cell lines of various cancer types were obtained from ATCC. Total RNAs were prepared using the TRI Reagent (Molecular Research Center). They were reverse transcribed with Superscript II (Gibco/BRL) to generate cDNAs. Nested PCR amplifications of the cDNAs from 92 cell lines were performed to prepare 10 sets of B112 amplicons for mutation screening according to the protocol of Teng et al. (1997). The PCR primers used are listed in Table 2. The PCR primers used for nested amplifications are listed in Table 3. Greater than 95% coverage of the coding sequence of B112 was obtained for every tumor cell line screened. All detected mutations were confirmed by sequencing a newly amplified product. Homozygous deletion searches of the genomic DNAs were done with the following primer pairs: B112-hdF100 (5-GGCGGTATTTGACCTGTCCA-3' SEQ ID NO:7) and B112-hdR301 (5'-CTTGCTTAATATGCTCCACAC-3' SEQ ID NO:8). A reaction was scored positive when the PCR product of expected size appeared.

To determine if the CtIP gene is mutated, genomic DNAs and cDNAs from 92 tumor cell lines of different tissue types were screened for homozygous deletions and coding mutations, respectively. No homozygous deletion was observed with this set of DNA samples. However, an apparent loss of heterozygosity or homozygosity was found at this gene locus in eight cell lines when the cDNA sequences were examined. Five missense and twelve silent variants were found in the coding region of CtIP (Table 4). In the pancreatic tumor cell line, BxPC3, a nonconserved amino acid change at codon 337 was identified. This cell line also has an apparent LOH as the wild type allele of CtIP was not observed. The predicted effects of all base changes are summarized in Table 4.

EXAMPLE 5

Generation of Polyclonal Antibody against CtIP

Segments of CtIP coding sequence are expressed as fusion protein in E. Coli. The overexpressed protein is purified by gel elution and used to immunize rabbits and mice using a procedure similar to the one described by Harlow and Lane, 1988. This procedure has been shown to generate Abs against various other proteins (for example, see Kraemer et al., 1993).

Briefly, a stretch of CtIP coding sequence is cloned as a fusion protein in plasmid PET5A (Novagen, Inc., Madison, Wis.). After induction with IPTG, the overexpression of a fusion protein with the expected molecular weight is verified by SDS/PAGE. Fusion protein is purified from the gel by electroelution. Identification of the protein as the CtIP fusion product is verified by protein

TABLE 2

| Primer Name | Sequence | SEQ ID NO. |
|---|---|---|
| B112.1A | CAC AGC CTC AGA AAG TGC TCG | 9 |
| B112.1P | AAG TGT TGC TAA AAG GGA GTG | 10 |
| B112.1B | GTT TTC CCA GTC ACG ACG GAG GCG GTA TTT GAC CTG TCC | 11 |
| B112.1Q | AGG AAA CAG CTA TGA CCA TCT TCA GTT ACT GCA CAG CGA T | 12 |
| B112.1C | GTT TTC CCA GTC ACG ACG AAA ATC AAC AGC TGA GGG AAC A | 13 |
| B112.1R | AGG AAA CAG CTA TGA CCA TGT TCT CCT TTC TTC GTA GCC G | 14 |
| B112.1D | GTT TTC CCA GTC ACG ACG CAC CGA TAA CAG CCT TCT CAT | 15 |

TABLE 2-continued

| Primer Name | Sequence | SEQ ID NO. |
|---|---|---|
| B112.1S | AGG AAA CAG CTA TGA CCA TTG GGA CCT TGA GTT TCA GAT T | 16 |
| B112.1E | GTT TTC CCA GTC ACG ACG ACC CCT GAT AAG TCA TCT TTT A | 17 |
| B112.1T | AGG AAA CAG CTA TGA CCA TGG GAC AAA CTT GTA TTC AAA TC | 18 |
| B112.2A | AGA TTC TAC TTC AAA GAC TCC T | 19 |
| B112.2P | TTA TCA CCA TGA GTG TGT AGT T | 20 |
| B112.2B | GTT TTC CCA GTC ACG ACG CGA GTG TCA TCT CCT GTA TTT | 21 |
| B112.2Q | AGG AAA CAG CTA TGA CCA TGG CAG CTT ACT TCA TGT TCA C | 22 |
| B112.2C | GTT TTC CCA GTC ACG ACG GAT AAA CAT TTG GAG CCC CTG | 23 |
| B112.2R | AGG AAA CAG CTA TGA CCA TAA CGT GCA GTT GCC ATC TGA G | 24 |
| B112.2D | GTT TTC CCA GTC ACG ACG AGG CAA GTG ACT CTT TAT GAG | 25 |
| B112.2S | AGG AAA CAG CTA TGA CCA TAT CTT GGT TGT TTT GTA GAG AC | 26 |
| B112.2E | GTT TTC CCA GTC ACG ACG AAA AAT ACA AAC CAG GTC AGA C | 27 |
| B112.2T | AGG AAA CAG CTA TGA CCA TTC TGC AAA ACA GGA TTC ATA C | 28 |
| B112.2I | TCA TTT TCT GGC GTT AAC CGG CT | 29 |
| B112.2X | GTC TGG AGA GCA TTT ATT CAA GGG | 30 |
| B112.2J | GTT TTC CCA GTC ACG ACG GGA AGG AAA TCA CAA GAA ACA GCC | 31 |
| B112.2Y | AGG AAA CAG CTA TGA CCA TGG GCA CTA TCT TCA GAT TTT GAT C | 32 |
| B112.2K | GTT TTC CCA GTC ACG ACG TCA AAG ACT CCT CCT CAA GAA G | 33 |
| B112.2Z | AGG AAA CAG CTA TGA CCA TGA TGA CTG GAT AAT GAT CTT GTT C | 34 |
| B112.3A | AAA TGA AGA AGC AAG AGC AGA A | 35 |
| B112.3P | AGT TAG AGT GCA AAA TGA AAG C | 36 |
| B112.3B | GTT TTC CCA GTC ACG ACG GCA GAA GGG AGA AAA AAG TTC | 37 |
| B112.3Q | AGG AAA CAG CTA TGA CCA TTG TCT TGA GCA GGA AGC AAA T | 38 |
| B112.3C | GTT TTC CCA GTC ACG ACG AGA AGA AAA CTG CTT GGG CAC A | 39 |
| B112.3R | AGG AAA CAG CTA TGA CCA TAA ACT GTC CTT CAT CCT TCT GT | 40 |

TABLE 3

| Primary Amplicon | Secondary Amplicon |
|---|---|
| B112.1A-B112.1P | B112.1B-B112.1Q |
|  | B112.1C-B112.1R |
|  | B112.1D-B112.1S |
|  | B112.1E-B112.1T |
| B112.2A-B112.2P | B112.2B-B112.2Q |
|  | B112.2C-B112.2R |
|  | B112.2D-B112.2S |
|  | B112.2E-B112.2T |
| B112.2I-B112.2X | B112.2J-B112.2Y |
|  | B112.2K-B112.2Z |
| B112.3A-B112.3P | B112.3B-B112.3Q |
|  | B112.3C-B112.3R |

TABLE 4

| Cell Line | Type | Alteration | Codon | Predicted Effect |
|---|---|---|---|---|
| BxPC3 | Pancreas | 1009 A > G | 337 | Lys > Glu |
| HCT-15 | Colon | 1180 G + A | 394 | Val + Met |
| HCT-15 | Colon | 1306 C + T | 436 | Pro + Ser |
| NCI-H1155 | Lung | 1644 T > C | 548 | Silent |
| NIH-ovcar3 | Ovarian | 1766 G > A | 589 | Arg > His |
| ZR75-30 | Breast | 2115 G > A | 705 | Silent |
| OV1063 | Ovarian | 2115 G + A | 705 | Silent |
| NCI-H2122 | Lung | 2456 A + G | 819 | Tyr + Ser |
| HS578T | Breast | 2565 T + G | 855 | Silent |

A representation as A > G indicates that the cell line is homozygous or hemizygous for this alteration
A representation as G + A indicates that the cell line is heterozygous for this alteration sequencing at the N-terminus. Next, the purified protein is used as immunogen in rabbits. Rabbits are immunized with 100 μg of the protein in complete Freund's adjuvant and boosted twice in 3 week intervals, first with 100 μg of immunogen in incomplete Freund's adjuvant followed by 100 μg of immunogen in PBS. Antibody containing serum is collected two weeks thereafter.

This procedure is repeated to generate antibodies against the mutant forms of the CtIP gene product. These antibodies, in conjunction with antibodies to wild type CtIP, are used to detect the presence and the relative level of the mutant forms in various tissues and biological fluids.

EXAMPLE 6

Generation of Polyclonal Antibody against CtIP-CtIP Interacting Protein Complex

CtIP is capable of binding to certain proteins, e.g., BRCA1. A complex of the two proteins is prepared, e.g., by mixing purified preparations of each of the two proteins. If desired, the protein complex can be stabilized by cross-linking the proteins in the complex by methods known to those of skill in the art. The protein complex is used to immunize rabbits and mice using a procedure similar to the one described by Harlow and Lane, 1988. This procedure has been shown to generate Abs against various other proteins (for example, see Kraemer et al., 1993).

Briefly, the purified protein complex is used as immunogen in rabbits. Rabbits are immunized with 100 μg of the protein in complete Freund's adjuvant and boosted twice in 3 week intervals, first with 100 μg of immunogen in incomplete Freund's adjuvant followed by 100 μg of immunogen in PBS. Antibody containing serum is collected two weeks thereafter.

This procedure is repeated to generate antibodies against forms of the complex which comprise mutant CtIP or mutant CtIP interacting protein (e.g., mutant BRCA1). These antibodies, in conjunction with antibodies to wild type CtIP or CtIP interacting protein (e.g., BRCA1), are used to detect the presence and the relative level of the mutant forms in various tissues and biological fluids.

EXAMPLE 7

Generation of Monoclonal Antibodies Specific for CtIP

Monoclonal antibodies are generated according to the following protocol. Mice are immunized with immunogen comprising intact CtIP or CtIP peptides (wild type or mutant) conjugated to keyhole limpet hemocyanin using glutaraldehyde or EDC as is well known.

The immunogen is mixed with an adjuvant. Each mouse receives four injections of 10 to 100 μg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of $2 \times 10^5$ cells/well in 96 well tissue culture plates. Individual wells are examined for growth and the supernatants of wells with growth are tested for the presence of CtIP specific antibodies by ELISA or RIA using wild type or mutant CtIP target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

EXAMPLE 8

Generation of Monoclonal Antibodies Specific for CtIP-CtIP Interacting Protein Complex Monoclonal antibodies are generated according to the following protocol. Mice are immunized with immunogen comprising CtIP-CtIP interacting protein complexes (wild type or mutant) conjugated to keyhole limpet hemocyanin using glutaraldehyde or EDC as is well known. The complexes may be stabilized by cross-linking.

The immunogen is mixed with an adjuvant. Each mouse receives four injections of 10 to 100 μg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein, 1975. Briefly, P3.65.3 myeloma cells (American Type Culture Collection, Rockville, Md.) are fused with immune spleen cells using polyethylene glycol as described by Harlow and Lane, 1988. Cells are plated at a density of $2 \times 10^5$ cells/well in 96 well tissue culture plates. Individual wells are examined for growth and the supernatants of wells with growth are tested for the presence of CtIP-CtIP interacting protein complex specific antibodies by ELISA or RIA using wild type or mutant CtIP-CtIP interacting protein complexes as target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development. Antibodies are tested for binding to CtIP alone or to CtIP interacting protein alone to determine which are specific for the complex as opposed to binding to the individual proteins.

EXAMPLE 9

Sandwich Assay for CtIP

Monoclonal antibody is attached to a solid surface such as a plate, tube, bead or particle. Preferably, the antibody is attached to the well surface of a 96-well ELISA plate. 100 μL sample (e.g., serum, urine, tissue cytosol) containing the CtIP peptide/protein (wild-type or mutants) is added to the solid phase antibody. The sample is incubated for 2 hrs at room temperature. Next the sample fluid is decanted, and the solid phase is washed with buffer to remove unbound material. 100 μL of a second monoclonal antibody (to a different determinant on the CtIP peptide/protein) is added to the solid phase. This antibody is labeled with a detector molecule (e.g., $^{125}$I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of CtIP peptide/protein present in the sample, is quantified. Separate assays are performed using monoclonal antibodies which are specific for the wild-type CtIP as well as monoclonal antibodies specific for each of the mutations identified in CtIP.

EXAMPLE 10

Drug Screening

The invention is useful in screening for drugs which can overcome mutations in CtIP and also mutations in BRCA1. The knowledge that CtIP and BRCA1 form a complex is useful in designing such assays. If a mutation is present in either CtIP or in BRCA1 which prevents the CtIP-BRCA1 complex from forming, drugs may be screened which will overcome the mutation and allow the protein complex to form and to be active. Such screening assays can be, e.g., a yeast two hybrid assay which is dependent upon two proteins interacting. In such an assay, the presence of a mutant protein may show no activity or low activity in such an assay, while the presence of a useful drug will result in formation of a proper complex which results in activity in the assay.

A simple binding assay which shows the binding, i.e., formation of a complex, can similarly be used as outlined above. Useful drugs will increase the formation of CtIP-BRCA1 complexes. Antibodies may also be used to monitor the amount of complex present. Antibodies specific for the complex are especially useful. If the presence of a drug increases the amount of complex present then the drug is a good candidate for treating the cancer which is a result of the mutation in either the CtIP or the BRCA1.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Anand, R. (1992). *Techniques for the Analysis of Complex Genomes,* (Academic Press).
Anderson, et al. (1980). Proc. Natl. Acad. Sci. USA 77, 5399–5403.
Ausubel, F. M., et al. (1992). Current Protocols in Molecular Biology, (J. Wiley and Sons, N.Y.)
Bartel, P. et al. (1996). "A protein linkage map of *Escherichia coli* bacteriophage T7", Nature Genet. 12, 72–77.
Bartel, P. L. and Fields, S. (1995). "Analyzing protein—protein intereactions using the yeast two hybrid system", Methods in Enzymology 254, 241–263.
Beaucage and Carruthers (1981). Tetra. Letts. 22, 1859–1862.
Berkner, et al. (1988). BioTechniques 6, 6.16–629.
Berkner (1992). Curr. Top. Microbiol. Immunol. 158, 39–61.
Borman, S. (1996). Chemical & Engineering News, December 9 issue, pp. 42–43.
Brandyopadhyay and Temin (1984). Mol. Cell. Biol. 4, 749–754.
Breakfield and Geller (1987). Mol. Neurobiol. 1, 337–371.
Breeden, L., and Naysmyth, K. (1985). "Regulation of the yeast HO gene", Cold Spring Harbour Symp. Quant. Biol. 50, 643–650.
Brinster, et al. (1981). Cell 27, 223–231.
Buchschacher and Panganiban (1992). J. Virol. 66, 2731–2739.
Callebaut, I., and Mornon, J. -P. (1997). "From BRCA1 to RAP1: a widespread BRCT module closely associated with DNA repair", FEBS Letters 400, 25–30.
Cannon-Albright, L. A., and Skolnick M. H. (1996). "The genetics of familial breast cancer.", Semin. Oncol. 23, 1–5.
Capecchi, M. R. (1989). Science 244, 1288.
Cariello (1988). Human Genetics 42, 726.
Chapman, M. S., and Verma, I. (1996). "Transcriptional activation by BRCA1", Nature 382, 678–679.
Chee, M., et al. (1996). Science 274, 610–614.
Chen, Y., et al. (1995). "Aberrant subcellular localization of BRCA1 in breast cancer." Science 270, 789–791.
Chen, C. -F., et al. (1996a). "The nuclear localization sequences of the BRCA1 protein interact with the importin-α subunit of the nuclear transport signal receptor." J. Biol. Chem. 271, 32863–32868.
Chen. Y., et al. (1996b). "BRCA1 is a 220-kDa nuclear phosphoprotein that is expressed and phosphorylated in a cell cycle-dependent manner", Cancer Res. 56, 3168–3172.
Compton, J. (1991). "Nucleic acid sequence-based amplification." Nature 350, 91–92.
Conner, B. J., et al. (1983). Proc. Natl. Acad. Sci. USA 80, 278–282.
Constantini and Lacy (1981). Nature 294, 92–94.
Cotten, M., et al. (1990). Transferrin-polycation-mediated introduction of DNA into human leukemic cells: stimulation by agents that affect the survival of transfected DNA or modulate transferrin receptor levels. Proc. Natl. Acad. Sci. USA 87, 4033–4037.
Cotton, R. G., et al. (1988). Reactivity of cytosine and thymine in single-base-pair mismatches with hydroxylamine and osmium tetroxide and its application to the study of mutations. Proc. Natl. Acad. Sci. USA 85,4397–4401.
Curiel, et al. (1991a). Hum. Gene Ther. 3, 147–154.
Curiel, et al. (1991b). Proc. Natl. Acad. Sci. USA 88, 8850–8854.
Deutscher, M. (1990). Meth. Enzymology 182 (Academic Press, San Diego, Calif.).
Donehower, L. A., et al. (1992). Nature 356, 215.
Editorial (1996). Nature Genetics 14, 367–370.
Elghanian, R., et al. (1997). Science 277, 1078–1081.
*Enhancers and Eukaryotic Gene Expression,* Cold Spring Harbor Press, Cold Spring Harbor, N.Y. (1983).
Erickson, J., et al. (1990). Science 249, 527–533.
Fahy, E., et al. (1991). "Self-sustained sequence replication (3SR): an isothermal transcription-based amplification system alternative to PCR." PCR Methods Appl. 1, 25–33.
Felgner, et al. (1987). Proc. Natl. Acad. Sci. USA 84, 7413–7417.
Fiers, et al. (1978). Nature 273, 113.
Fink, et al. (1992). Hum. Gene Ther. 3, 11–19.
Finkelstein, J., et al. (1990). Genomics 7, 167–172.
Fodor, S. P. A. (1997). DNA Sequencing. Massively Parallel Genomics. Science 277, 393–395.
Freese, et al. (1 990). Biochem. Pharmacol. 40, 2189–2199.
Friedman, T. (1991). In Therapy for Genetic Diseases, T. Friedman, ed., Oxford University Press, pp. 105–121.
Gietz, R. D., et al. (1995). "Studies on the transformation of intact yeast cells by the LiAc/SS-DNA/PEG procedure", Yeast 11, 355–360.
Glover, D. (1985). *DNA Cloning,* I and II (Oxford Press).
Goding (1986). *Monoclonal Antibodies: Principles and Practice;* 2d ed. (Academic Press, N.Y.).
Godowski, et al. (1988). Science 241, 812–816.
Gordon, et al. (1980). Proc. Natl. Acad. Sci. USA 77, 7380–7384.

Gorlick, D. (1997). "Nuclear protein import", Current Opinion in Cell Biology 9, 412–419.
Gorziglia and Kapikian (1992). J. Virol. 66, 4407–4412.
Graham and van der Eb (1973). Virology 52, 456–467.
Grompe, M. (1993). Nature Genetics 5, 111–117.
Grompe, M., et al. (1989). Proc. Natl. Acad. Sci. USA 86, 5855–5892.
Guthrie, G. and Fink, G. R. (1991). *Guide to Yeast Genetics and Molecular Biology* (Academic Press).
Hacia, J. G., et al. (1996). Nature Genetics 14, 441–447.
Hakem, R., et al. (1996). "The tumor suppressor gene Brca1 is required for embryonic cellular proliferation in the mouse", Cell 85, 1009–1023.
Harlow and Lane (1988). Antibodies: A Laboratory Manual (Cold Spring Harbor Laboratory, Cold Spring Harbor, N.Y.).
Hasty, P., K., et al. (1991). Nature 350, 243.
Helseth, et al. (1990). J. Virol. 64, 2416–2420.
Hicks, R. G. and Raikhel, N. V. (1995). "Protein import into the nucleus: an integrated view", Annual Review of Cell and Developmental Biology 11, 155–188.
Hodgson, J. (1991). Bio/Technology 9, 19–21.
Huse, et al. (1989). Science 246, 1275–1281.
Innis, et al. (1990). *PCR Protocols: A Guide to Methods and Applications* (Academic Press, San Diego, Calif.).
Jablonski, E., et al. (1986). Nucl. Acids Res. 14, 6115–6128.
Jakoby, W. B. and Pastan, I. H. (eds.) (1979). Cell Culture. Methods in Enzymology, volume 58 (Academic Press, Inc., Harcourt Brace Jovanovich (New York)).
Jin, Y., et al. (1997). "Cell cycle-dependent colocalization of BARD1 and BRCA1 proteins in discrete nuclear domains." Proc. Natl. Acad. Sci. USA 94, 12075–12080.
Johnson, et al. (1992). J. Virol. 66, 2952–2965.
Kaneda, et al. (1989). J. Biol. Chem. 264, 12126–12129.
Kanehisa (1984). Nucl. Acids Res. 12, 203–213.
Kinszler, K. W., et al. (1991). Science 251, 1366–1370.
Kohler, G. and Milstein, C. (1975). Nature 256, 495–497.
Koonin, E. V., et al. (1996). "BRCA1 protein products: functional motifs", Nature Genet. 13, 266–268.
Kraemer, F. B. et al. (1993). J. Lipid Res. 34, 663–672.
Kubo, T., et al. (1988). FEBS Letts. 241, 119.
Landegren, et al. (1988). Science 242, 229.
Larson, J. S., et al. (1997). "A BRCA1 mutant alters G2-M cell cycle control in human mammary epithelial cells", Cancer Res. 57, 3351–3355.
Lim, et al. (1992). Circulation 83, 2007–2011.
Lipshutz, R. J., et al. (1995). Biotechniques 19, 442–447.
Lockhart, D. J., et al. (1996). Nature Biotechnology 14, 1675–1680.
Madzak, et al. (1992). J. Gen. Virol. 73, 1533–1536.
Maldonado, E., et al. (1996). "A human RNA polymerase II complex associated with SRB and DNA-repair proteins", Nature 381, 86–89.
Maniatis, T. et al. (1982). *Molecular Cloning: A Laboratory Manual* (Cold Spring Harbor Laboratory, Cold Spring Harbor, N.Y.).
Mann and Baltimore (1985). J. Virol. 54, 401–407.
Margolskee (1992). Curr. Top. Microbiol. Immunol. 158, 67–90.
Martin, R., et al. (1990). BioTechniques 9, 762–768.
Matteucci, M. D. and Caruthers, M. H. (1981). J. Am. Chem. Soc. 103, 3185.
Matthews and Kricka (1988). Anal. Biochem. 169, 1.
McAllister, K. A., et al. (1997). "Characterization of the rat and mouse homologues of the BRCA2 breast cancer susceptibility gene", Cancer Res. 57, 3121–3125.
Merrifield (1963). J. Am. Chem. Soc. 85, 2149–2156.
Metzger, et al. (1988). Nature 334, 31–36.
Miki, Y., et al. (1994). Science 266, 66–71.
Miller (1992). Curr. Top. Microbiol. Immunol. 158, 1–24.
Miller, et al. (1985). Mol. Cell. Biol. 5, 431–437.
Miller, et al. (1988). J. Virol. 62, 4337–4345.
Modrich, P. (1991). Ann. Rev. Genet. 25, 229–253.
Mombaerts, P., et al. (1992). Cell 68, 869.
Monteiro, A. N. A., et al. (1996). "Evidence for a transcriptional activation function of BRCA1 C-terminal region", Proc. Natl. Acad. Sci. USA 93, 13595–13599.
Moss (1992). Curr. Top. Microbiol. Immunol. 158, 25–38.
Muzyczka (1992). Curr. Top. Microbiol. Immunol. 158, 97–123.
Nabel, et al. (1990). Science 249, 1285–1288.
Nabel (1992). Hum. Gene Ther. 3, 399–410.
Newton, C. R., et al. (1989). Nucl. Acids Res. 17, 2503–2516.
Nguyen, Q., et al. (1992). BioTechniques 13, 116–123.
Novack, et al. (1986). Proc. Natl. Acad. Sci. USA 83, 586.
Ohi, et al. (1990). Gene 89, 279–282.
Orita, M., et al. (1989). Detection of polymorphisms of human DNA by gel electrophoresis as single strand conformation polymorphisms. Proc. Natl. Acad. Sci. USA 86, 2766–2770.
Page, et al. (1990). J. Virol. 64, 5370–5276.
Pellicer, et al. (1980). Science 209, 1414–1422.
Petropoulos, et al. (1992). J. Virol. 66, 3391–3397.
Philpott, K. L., et al. (1992). Science 256, 1448.
Quantin, et al. (1992). Proc. Natl. Acad. Sci. USA 89, 2581–2584.
Rano and Kidd (1989). Nucl. Acids Res. 17, 8392.
Rigby, P. W. J., et al. (1977). J. Mol. Biol. 113, 237–251.
Rosenfeld, et al. (1992). Cell 68, 143–155.
Sambrook, J., et al. (1989). *Molecular Cloning: A Laboratory Manual, 2nd Ed.* (Cold Spring Harbor Laboratory, Cold Spring Harbor, N.Y.).
Sande, S., and Privalsky, M. L. (1996). "Identification of TRACs (T3 Receptor-Associating Cofactors), a family of cofactors that associate with, and modulate the activity of, nuclear hormone receptors", Molecular Endocrin. 10, 813–825.
Sanger, F., et al. (1977). "DNA sequencing with chain-terminating inhibitors", Proc. Natl. Acad. Sci. USA 74, 5463–5466.
Schaeper, U., et al. (1995). "Molecular cloning and characterization of a cellular phosphoprotein that interacts with a conserved C-terminal domain of adenovirus E1A involved in negative modulation of oncogenic transformation", Proc. Natl. Acad. Sci. USA 92, 10467–10471.
Scharf (1986). Science 233, 1076.
Scopes, R. (1982). *Protein Purification: Principles and Practice,* (Springer-Verlag, N.Y.).
Scully, R., et al. (1997a). "Dynamic changes of BRCA1 subnuclear location and phosphorylation state are initiated by DNA damage." Cell 90, 425–435.
Scully, R., et al. (1997b). "Association of BRCA1 with Rad51 in mitotic and meiotic cells", Cell 88, 265–275.
Scully, R., et al. (1997c). "BRCA1 is a component of the RNA polymerase II holoenzyme", Proc. Natl. Acad. Sci. USA 94, 5605–5610.
Shao, N., et al. (1996). "Induction of apoptosis by the tumor suppressor protein BRCA1", Oncogene 13, 1–7.
Sharan, S. K., et al. (1997). "Embryonic lethality and radiation hypersensitivity mediated by Rad51 in mice lacking BRCA2", Nature 386, 804–810.
Shattuck-Eidens, D., et al. (1995). "A collaborative survey of 80 mutations in the BRCA1 breast and ovarian cancer susceptibility gene. Implications for presymptomatic testing and screening.", JAMA 15, 535–541.

Sheffield, V. C., et al. (1989). Proc. Natl. Acad. Sci. USA 86, 232–236.

Sheffield, V. C., et al., (1991). Am. J. Hum. Genet. 49, 699–706.

Shenk, T. E., et al. (1975). Biochemical method for mapping mutational alterations in DNA with S1 nuclease; the location of deletions and temperature-sensitive mutations in simian virus 40. Proc. Natl. Acad. Sci. USA 72, 989–993.

Shimada, et al. (1991). J. Clin. Invest. 88, 1043–1047.

Shinkai, Y., et al. (1992). Cell 68, 855.

Shinohara, A., et al. (1992). "Rad51 protein involved in repair and recombination in *Saccharomyces cerevisiae* is a RecA-like protein." Cell 69, 457–470.

Shinohara, A., et al. (1993). "Cloning of human, mouse and fission yeast recombination genes homologous to RAD51 and recA", Nat Genet. 4, 239–243.

Shoemaker, D. D., et al. (1996). Nature Genetics 14, 450–456.

Snouwaert, J. N., et al. (1992). Science 257, 1083.

Sobol, H., et al. (1996). "Truncation at conserved terminal regions of BRCA1 protein is associated with highly proliferating hereditary breast cancers", Cancer Res. 56, 3216–3219.

Sollerbrant, K., et al. (1996). "The CtBP binding domain in the adenovirus E1A protein controls CR1-dependent transactivation", Nucleic Acids Res. 24, 2578–2584.

Somasundaram, K., et al. (1997). "Arrest of the cell cycle by the tumour-suppressor BRCA1 requires the CDK-inhibitor p21WAF1/CiP1", Nature 389,187–190.

Sorge, et al. (1984). Mol. Cell. Biol. 4, 1730–1737.

Spargo, C. A., et al. (1996). "Detection of M. tuberculosis DNA using thermophilic strand displacement amplification." Mol. Cell. Probes 10, 247–256.

Stewart, et al. (1992). Hum. Gene Ther. 3, 267–275.

Stratford-Perricaudet, et al. (1990). Hum. Gene Ther. 1, 241–256.

Tavtigian, S. V., et al. (1996). "The complete BRCA2 gene and mutations in chromosome 13q-linked kindreds." Nature Genet. 12, 333–337.

Teng, D. H. -F., et al. (1997). "Human mitogen-activated protein kinase kinase 4 as a candidate tumor suppressor", Cancer Res. 57, 4177–4182.

Thomas, J. E., et al. (1996). "Subcellular localization and analysis of apparent 180-kDa and 220 kDa proteins of the breast cancer susceptibility gene, BRCA1." J. Biol. Chem. 271, 28630–28635.

Valancius, V. and Smithies, 0. (1991). Mol. Cell Biol. 11, 1402.

Wagner, et al. (1991). Proc. Natl. Acad. Sci. USA 88, 4255–4259.

Wagner, et al. (1990). Proc. Natl. Acad. Sci. USA 87, 3410–3414.

Walker, G. T., et al. (1992). "Strand displacement amplification—an isothermal, in vitro DNA amplification technique." Nucl. Acids Res. 20, 1691–1696.

Wang and Huang (1989). Biochemistry 28, 9508–9514.

Wartell, R. M., et al. (1990). Nucl. Acids Res. 18, 2699–2705.

Wells, J. A. (1991). Methods in Enzymol. 202,390–411.

Wetmur and Davidson (1968). J. Mol. Biol. 31, 349–370.

White, M. B., et al. (1992). Genomics 12, 301–306.

White and Lalouel (1988). Ann. Rev. Genet. 22, 259–279.

Wilkinson, et al. (1992). Nucleic Acids Res. 20, 2233–2239.

Wilson, C. A., et al. (1997). "Differential subcellular localization, expression and biological toxicity of BRCA1 and the splice variant BRCA1-Δ11b." Oncogene 14, 1–16.

Wolff, et al. (1990). Science 247, 1465–1468.

Wolff, et al. (1991). BioTechniques 11, 474–485.

Wong, A. K. C., et al. (1997). "RAD51 interacts with the evolutionary conserved BRC motifs in the human breast cancer susceptibility gene brca2", J. Biol. Chem. (in press).

Wu, et al. (1989a). Genomics 4:560–569.

Wu, et al. (1989b). J. Biol. Chem. 264, 16985–16987.

Wu, et al. (1991). J. Biol. Chem. 266, 14338–14342.

Wu, L. C., et al. (1996). "Identification of a RING protein that can interact in vivo with the BRCA1 gene product." Nat. Genet. 14, 430–440.

Zenke, et al. (1990). Proc. Natl. Acad. Sci. USA 87, 3655–3659.

Patents and Patent Applications:

European Patent Application Publication No. 0332435.

EPO Publication No. 225,807.

Geysen, H., PCT published application WO 84/03564, published Sep. 13, 1984

Hitzeman et al., EP 73,675A.

PCT published application WO 93/07282.

U.S. Pat. No. 3,817,837

U.S. Pat. No. 3,850,752

U.S. Pat. No. 3,939,350

U.S. Pat. No. 3,996,345

U.S. Pat. No. 4,275,149

U.S. Pat. No. 4,277,437

U.S. Pat. No. 4,366,241

U.S. Pat. No. 4,376,110.

U.S. Pat. No. 4,486,530.

U.S. Pat. No. 4,683,195

U.S. Pat. No. 4,683,202

U.S. Pat. No. 4,816,567

U.S. Pat. No. 4,868,105.

U.S. Pat. No. 5,252,479.

U.S. Pat. No. 5,270,184.

U.S. Pat. No. 5,409,818.

U.S. Pat. No. 5,455,166.

What is claimed is:

1. An isolated protein comprising protein of an amino acid sequence of SEQ ID NO:6.

2. An isolated mutant CtIP which cannot form a complex with BRCA1 with which wild-type CtIP does form a complex wherein said wild-type protein is BRCA1.

3. An isolated protein complex comprising CtIP and BRCA1.

4. The isolated protein complex of claim 3 wherein said CtIP contains an alteration.

5. The isolated protein complex of claim 4 wherein said alteration is selected from the group consisting of Glu at amino acid residue 337, Met at amino acid residue 394, Ser at amino acid residue 436, His at amino acid residue 589 and Ser at amino acid residue 819.

6. The isolated protein complex of claim 3 wherein said BRCA1 contains an alteration.

7. A protein complex comprising a fragment of CtIP and a fragment of BRCA1.

8. The protein complex of claim 7 wherein said fragment of CtIP comprises amino acid residues 324–584.

9. The protein complex of claim 7 wherein said fragment of BRCA1 comprises amino acid residues 1602–1863.

10. The protein complex of claim 7 wherein said CtIP comprises an alteration.

11. The protein complex of claim 10 wherein said alteration is a Glu at amino acid residue 337, a Met at amino acid residue 394, a Ser at amino acid residue 436, a His at amino acid residue 589 or a Ser at amino acid residue 819.

12. The protein complex of claim 7 wherein said BRCA1 comprises an alteration.

13. An isolated protein consisting of an amino acid sequence of SEQ ID NO:6.

* * * * *